United States Patent
Reynolds et al.

(10) Patent No.: US 9,365,528 B2
(45) Date of Patent: Jun. 14, 2016

(54) DERIVATIVES OF SULINDAC, USE THEREOF AND PREPARATION THEREOF

(75) Inventors: Robert Reynolds, Birmingham, AL (US); Bini Mathew, Birmingham, AL (US); Gary A. Piazza, Mobile, AL (US)

(73) Assignee: Southern Research Institute, Birmingham, AL (US)

( * ) Notice: Subject to any disclaimer, the term of this patent is extended or adjusted under 35 U.S.C. 154(b) by 120 days.

(21) Appl. No.: 14/008,271

(22) PCT Filed: Mar. 30, 2012

(86) PCT No.: PCT/US2012/031507
§ 371 (c)(1),
(2), (4) Date: Dec. 16, 2013

(87) PCT Pub. No.: WO2012/135650
PCT Pub. Date: Oct. 4, 2012

(65) Prior Publication Data
US 2014/0094492 A1     Apr. 3, 2014

Related U.S. Application Data

(60) Provisional application No. 61/470,752, filed on Apr. 1, 2011.

(51) Int. Cl.
| | | |
|---|---|---|
| *C07D 307/52* | (2006.01) | |
| *C07D 213/38* | (2006.01) | |
| *C07C 211/19* | (2006.01) | |
| *C07D 295/13* | (2006.01) | |
| *C07D 211/26* | (2006.01) | |

(52) U.S. Cl.
CPC ............ *C07D 295/13* (2013.01); *C07C 211/19* (2013.01); *C07D 211/26* (2013.01); *C07D 213/38* (2013.01); *C07D 307/52* (2013.01)

(58) Field of Classification Search
None
See application file for complete search history.

(56) References Cited

U.S. PATENT DOCUMENTS

| | | | | |
|---|---|---|---|---|
| 3,532,752 A | * | 10/1970 | Shen | C07C 45/46 544/121 |
| 3,883,660 A | | 5/1975 | Shen et al. | |
| 5,093,356 A | * | 3/1992 | Girard | C07C 275/64 514/432 |
| 6,071,934 A | | 6/2000 | Sperl et al. | |
| 7,544,690 B2 | * | 6/2009 | Sekiguchi | C07D 239/95 514/231.5 |
| 2007/0244122 A1 | | 10/2007 | Piazza et al. | |
| 2008/0207751 A1 | | 8/2008 | Sparatore et al. | |

FOREIGN PATENT DOCUMENTS

| | | |
|---|---|---|
| CN | 101365461 A | 2/2009 |
| DE | 10163426 A1 | 7/2003 |
| JP | S43-21428 A | 9/1968 |
| JP | 2003-530437 A | 10/2003 |
| JP | 2004-315511 A | 11/2004 |
| JP | 2009-522364 A | 6/2009 |
| WO | WO-0178721 A1 | 10/2001 |
| WO | WO-2007/081694 A2 | 7/2007 |
| WO | WO-2011/140525 A2 | 11/2011 |

OTHER PUBLICATIONS

Notification of the First Office Action issued Aug. 12, 2014 in Chinese Appln 201280016113.X.
Supplementary European Search Report issued Aug. 29, 2014 in European Appln No. 12765957.
Gamerdinger et al., "Effects of sulindac sulfide on the membrane architecture and the activity of Y-secretase", Neuropharmacology, 54 (2008) 998-1005.
Japanese Office Action issued Dec. 1, 2015 in JP Application No. 2014-502842.

* cited by examiner

*Primary Examiner* — Yong Chu
(74) *Attorney, Agent, or Firm* — Polsinelli PC

(57) ABSTRACT

Derivatives of sulindac that lack cyclooxygenase inhibitory activity are provided along with pharmaceutical compositions containing them and use for treatment or prevention of cancer. The derivatives of sulindac are also suitable for treating chronic inflammatory conditions. A method for preparing the derivatives is also provided.

15 Claims, 2 Drawing Sheets

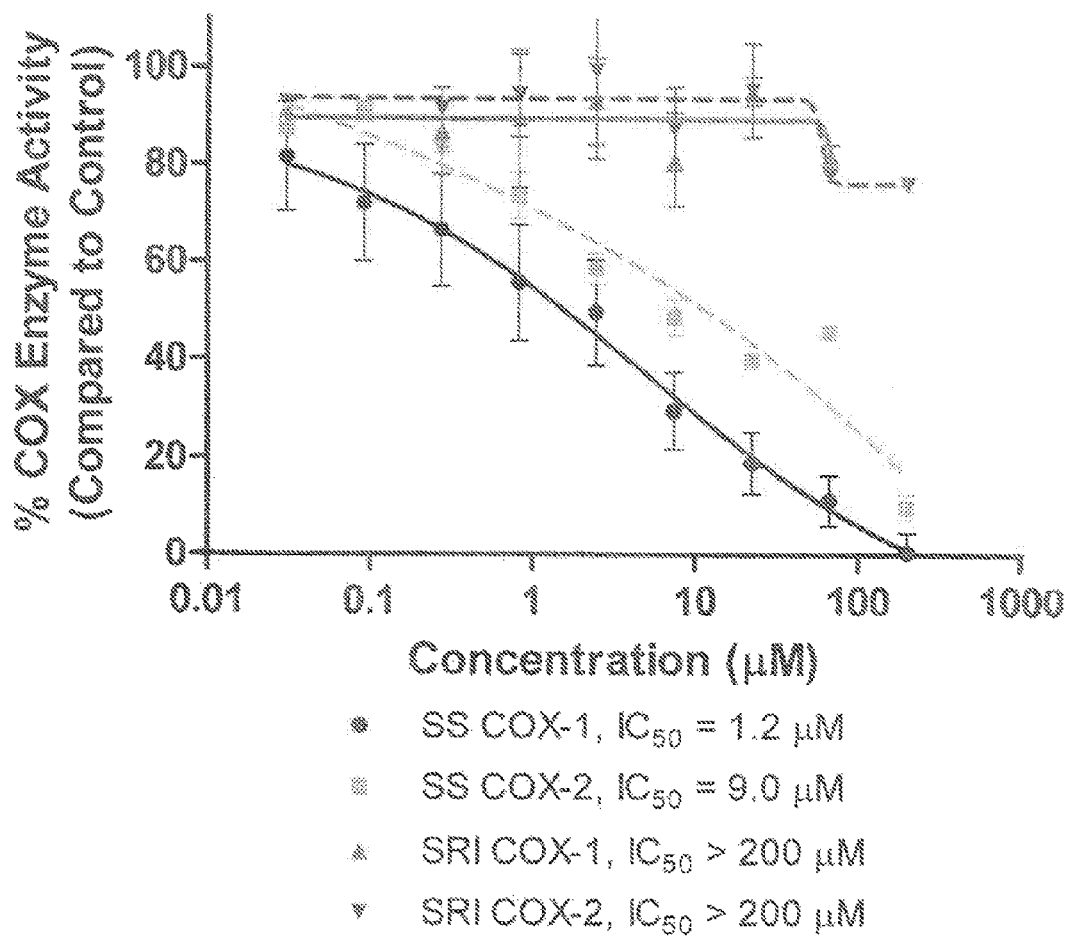
Figure 1. Cyclooxygenase (COX)-1 and -2 inhibitory activity of the NSAID, sulindac sulfide (SS), and lack of effect, an amino derivative of sulindac. Enzyme activity was measured using a colorimetric assay using recombinant COX enzymes. $IC_{50}$ values (50% inhibitory concentration) are listed for each COX isozyme.

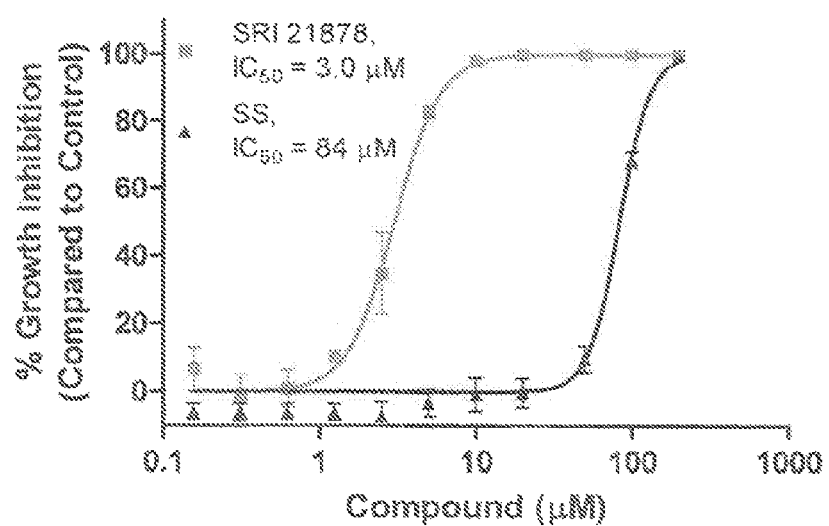
Figure 2. Tumor cell growth inhibitory activity of a trimethoxy amino derivative of sulindac and sulindac sulfide (SS) against the human MDA-MB-231 breast tumor cell line. Growth inhibitory activity was determined following 72 hours of treatment using a standard cell viability assay (Cell Titer Glo, Promega Corp).

DERIVATIVES OF SULINDAC, USE THEREOF AND PREPARATION THEREOF

CROSS REFERENCE TO RELATED APPLICATIONS

This application is a National Phase filing under 35 U.S.C. §371 of PCT/US2012/031507 filed on Mar. 30, 2012; and this application claims the benefit of U.S. Provisional Application No. 61/470,752 filed on Apr. 1, 2011; the entire contents of all are hereby incorporated by reference.

FEDERALLY SPONSORED RESEARCH AND DEVELOPMENT

This invention was supported by Grants CA 131378, CA 128021 and CA 148817 from the National Cancer Institute of the National Institutes of Health and the US Government has certain rights in the invention.

TECHNICAL FIELD

The present disclosure relates to certain derivatives of sulindac and especially amino derivatives of sulindac. The present disclosure also relates to pharmaceutical compositions comprising the disclosed derivatives of sulindac, as well as methods of using the disclosed derivatives of sulindac for the treatment and prevention of precancerous conditions and cancer in a mammal. The disclosed derivatives of sulindac are also suitable for treating chronic inflammatory conditions. The present disclosure also relates to methods for producing the disclosed compounds.

BACKGROUND

Even though significant advances have occurred in the treatment of cancer, it still remains a major health concern. Cancer has been reported as the leading cause of death in the United States with one of every four Americans likely to be diagnosed with the disease. By way of example, colorectal cancer is the third most commonly diagnosed cancer in the world that accounts for approximately 600,000 deaths per year. While a colonoscopy allows for the early detection of the disease and the identification of individuals who are at high risk of disease progression, the mortality rate from colorectal cancer has decreased only marginally in the last two decades (1). Additionally, certain lesions such as flat adenomas cannot be readily detected by a colonoscopy (2) and surgical management of adenomas in high risk individuals, such as with familial adenomatous polyposis (FAP) often requires complete or segmental removal of the colon (3). Given the slow progression of carcinogenesis and the limitations of colonoscopy, much research has focused on cancer chemoprevention to reduce the development and progression of colorectal cancer.

Included among the known chemotherapeutic drugs are carmustine, doxorubicin, methotrexate, paclitaxel, cyclophosphamide, procarbazine, and vinblastine, to name only a few. However, many chemotherapeutic drugs also produce undesirable side effects in the patient.

Certain nonsteroidal anti-inflammatory drugs (NSAIDs) have been recognized to have broad anticancer activity in animal models alone and in combination with chemotherapy or radiation. Representative examples include: Hial et al., "Alteration of tumor growth by aspirin and indomethacin: studies with two transplantable tumors in mouse" Eur. J. Pharm. 37: 367-376, 1976; Lynch et al., "Mechanism of inhibition of tumor growth by aspirin and indomethacin" Br. J. Cancer 38: 503-512, 1978; Bennett et al., "Increased survival of cancer-bearing mice treated with inhibitors of prostaglandin synthesis alone or with chemotherapy" Br. J. Cancer 45: 762-768, 1982; Pollard and Luckert "Prolonged antitumor effect of indomethacin on autochthonous intestinal tumors in rats" J. Natl. Cancer Inst. 70: 1103-1105, 1983; Fulton, "Inhibition of experimental metastasis with indomethacin: role of macrophages and natural killer cells" Prostaglandins: 35: 413-425, 1988; Moorghen et al., "The effect of sulindac on colonic tumor formation in dimethylhydrazine-treated mice" Acta histochemica 29: 195-199, 1990; and Moorghen et al., "A protective effect of sulindac against chemically-induced primary colonic tumours in mice" J. of Path. 156: 341-347.

Epidemiological studies have shown that long-term use of NSAIDs can significantly reduce the incidence and risk of death from colorectal cancer (4). In addition, certain prescription strength NSAIDs, such as sulindac can cause the regression and prevent recurrence of adenomas in individuals with FAP (5). The antineoplastic activity of NSAIDs is widely attributed to their cyclooxygenase (COX) inhibitory activity because prostaglandins are elevated in colon tumors (6) and a significant percentage of colon tumors express high levels of the inducible COX-2 isozyme (7). However, there is evidence that alternative mechanisms either contribute to or fully account for the colorectal cancer chemopreventive activity of NSAIDs (8-10). For example, the non-COX inhibitory sulfone metabolite of sulindac has been reported to inhibit the growth and induce apoptosis of colon tumor cell in vitro (11, 12) and suppress colon tumorigenesis in animal models (13-15). Sulindac sulfone (exisulind) was also shown to suppress adenoma formation in individuals with FAP or sporadic adenomas (16, 17), but did not receive FDA approval due to hepatotoxicity. The use of NSAIDs is associated with gastrointestinal, renal and cardiovascular toxicities from suppressing prostaglandin synthesis (18, 19).

Previous studies have shown that certain NSAIDs can decrease nuclear levels of β-catenin by inducing proteosomal degradation to inhibit the transcription of genes (e.g. cyclin D, survivin) that provide a survival advantage to allow for clonal expansion of neoplastic cells (20-22). Several groups have reported that sulindac sulfone can also induce the degradation of oncogenic β-catenin, which suggests that the underlying biochemical mechanism by which NSAIDs suppress β-catenin signaling may not require COX inhibition (22-24).

As mentioned above, Sulindac (Clinoril™) is a NSAID that has demonstrated anticancer activity. It has been recognized as having benefits for treating precancerous conditions as evidenced by a number of clinical trials in familial adenomatous polyposis patients which have shown the ability of sulindac to cause the regression of existing adenomas (size and number) and to inhibit new adenoma (polyp) formation. For example, see Waddell et al, "Sulindac for polyposis of the colon". J. of Surg. 157: 175-179, 1989; Labayle et al., "Sulindac causes regression of rectal polyps in familial adenomatous polyposis" Gastroenterology 101: 635-639, 1991; Nugent et al., "Randomized controlled trial of the effect of sulindac on duodenal and rectal polyposis and cell proliferation in patients with familial adenomatous polyposis" Br. J. Surg. 80: 1618-1619, 1993; Giardiello, et al., "Treatment of colonic and rectal adenomas with sulindac in familial adenomatous polyposis" N. Eng. J. Med 328: 1313-6, 1993; and Winde et al., "Complete reversion and prevention of rectal adenomas in colectomized patients with familial adenomatous polyposis by rectal low-dose sulindac maintenance treatment." Dis. Colon Rectum 38: 813-830, 1995.

The mechanism responsible for the anti-inflammatory efficacy and the toxicity of NSAIDs and COX-2 selective inhibitors (gastrointestinal, renal, hematological, cardiovascular) has been shown to involve cyclooxygenase COX-1 or COX-2 inhibition. Sulindac and certain other NSAIDs also have hepatic toxicity. For instance, see Vane, "Mode of action of aspirin and similar compounds" In Prostaglandin Synthetase Inhibitors, Eds Robinson, Raven Press, New York, N.Y., 1974; Eaker "Gastrointestinal injury related to the use of nonsteroidal anti-inflammatory drugs" Gastrointestinal Disease Today 6: 1-8, 1997; Wolfe et al., "Gastrointestinal toxicity of nonsteroidal anti-inflammatory drugs" N. Eng. J. Med 340: 1888-99, 1999; Palmer "Renal complications associated with use of nonsteroidal anti-inflammatory agents" J. Invest. Medicine 43: 516-533, 1995; Tarazi et al., "Sulindac-associated hepatic injury: analysis of 91 cases reported to the Food and Drug Administration" Gastroenterology 104: 569-574, 1993; and Mukherjee et al. "Risk of cardiovascular events associated with selective COX-2 inhibitors" JAMA 286: 954-959, 2001.

Most investigators attribute the mechanism for the anticancer activity of NSAIDs to anti-inflammatory activity involving COX inhibition, although there is some evidence for a COX-independent mechanism as mentioned below. For example, the activity of the sulfone metabolite of sulindac has been described which retains anticancer activity in preclinical and clinical trials but does not inhibit cyclooxygenase and displays less GI toxicity. See for example, Piazza et al., "Antineoplastic drugs sulindac sulfide and sulfone inhibit cell growth by inducing apoptosis" Cancer Res. 55: 3110-3116, 1995; Piazza et al., "Sulindac sulfone inhibits azoxymethane-induced colon carcinogenesis in rats without reducing prostaglandin levels" Cancer Res. 57: 2909-2915, 1997; Piazza et al., "Apoptosis primarily accounts for the growth inhibitory properties of sulindac metabolites and involves a mechanism that is independent of cyclooxygenase inhibition, cell cycle arrest, and p53 induction" Cancer Res. 57: 2452-2459, 1997; Piazza et al, "Exisulind a novel proapoptotic drug inhibits rat urinary bladder tumorigenesis" Cancer Res., 61: 3961-3968, 2001; and Chan "Nonsteroidal anti-inflammatory drugs, apoptosis, and colon-cancer chemoprevention" The Lancet Oncology 3: 166-174, 2002.

The mechanism responsible for the antineoplastic activity of sulindac sulfone has been previously reported to involve cyclic guanosine monophosphate (cGMP) phosphodiesterase (PDE) inhibition (23, 25). More recently, it has been reported that the COX inhibitory sulfide metabolite of sulindac and certain other NSAIDs also inhibit cGMP PDE, and that this activity is closely associated with their tumor cell growth inhibitory and apoptosis-inducing properties (26-28). Cyclic nucleotide PDEs are a large superfamily of enzymes responsible for regulating second messenger signaling by hydrolyzing the 3',5'-phosphodiester bond in cGMP and/or cAMP. There are at least eleven PDE isozyme family members having different substrate specificities, regulatory properties, tissue localization, and inhibitor sensitivity (29). PDE1, 2, 3, 10 and 11 are dual substrate-degrading isozymes, while PDE5, 6, and 9 are selective for cGMP and PDE4, 7, and 8 are cAMP selective. In addition, each isozyme family contains multiple isoforms or splice variants. Depending on the PDE isozyme content of the target cell population and inhibitor selectivity, PDE inhibitors can increase the magnitude and/or the duration of the cAMP and/or cGMP intracellular signal(s). Increasing cyclic nucleotide levels can induce specific signaling pathways, which, in the case of cGMP, can activate protein kinase G (PKG) to regulate cellular activity (30).

There are publications suggesting that certain chemical modifications to the carboxylic acid moiety of NSAIDs will result in improved safety (i.e., as prodrugs or by localized release of nitric oxide). For example, see Mahmud et al., "A unifying hypothesis for the mechanism of NSAID related gastrointestinal toxicity". Ann. Rheumatic Diseases 55: 211-213, 1996; Venuti et al., "Synthesis and biological evaluation of (N,N,N,-trialkylammonium)alkyl esters and thioesters of carboxylic acid nonsteroidal anti-inflammatory drugs" Pharmaceutical Research 6: 867-873, 1989; Salimbeni et al., "New esters of N-arylanthranilic acids" Farmaco 30: 276-86, 1975; and Elliot et al. "A nitric oxide-releasing nonsteroidal anti-inflammatory drug accelerates gastric ulcer healing in rats" Gastroenterology 109: 524-530, 1995.

In addition, U.S. Pat. Nos. 5,401,774, 6,166,053 and 6,200,771 suggest certain modifications to sulindac sulfone which is not a NSAID.

As another example, a series of amide and ester derivatives of indomethacin and meclofenamic acid involving modifications to the carboxylic acid moiety were described by Marnett et al. These compounds were described as having safety advantages over the parent NSAIDs based on selectivity for the cyclooxygenase-2 isozyme. However, anticancer activity was not described and modifications to improve anticancer efficacy (potency) were not described. For example, see Kalgutkar et al., "Biochemical based design of cyclooxygenase-2 (COX-2) inhibitors: facile conversion of nonsteroidal anti-inflammatory drugs to potent and highly selective COX-2 inhibitors" Proc. Natl. Acad. Sci. 97: 925-930, 2000; Kalgutkar et al. "Amide derivatives of meclofenamic acid as selective cyclooxygenase-2 inhibitors" Bioorganic and Medicinal Chemistry Letters 12: 521-524, 2002; Kalgutkar et al., "Ester and amide derivatives of the nonsteroidal anti-inflammatory drug, indomethacin, as selective cyclooxygenase-2 inhibitors" J. Med. Chem. 43: 2860-2870, 2000; U.S. Pat. No. 5,973,191 to Marnett and Kalgutkar "Selective inhibitors of prostaglandin endoperoxide synthetase-2"; and U.S. Pat. No. 5,475,021 to Marnett and Kalgutkar "Compounds and compositions for inhibition of cyclooxygenase activity".

More recently, various amide derivatives of sulindac have been disclosed in U.S. patent application Ser. No. 60/755,847 filed Jan. 4, 2006 and Ser. No. 11/649,373 filed Jan. 4, 2007, now U.S. Pat. No. 8,044,048 to Piazza et al. and assigned to Southern Research Institute, the assignee of the present application. However, during animal testing, modest metabolism of the amide linkage from at least one of the amide derivatives of sulindac was noted, producing sulindac sulfide a known COX 1 and COX 2 inhibitor. Production of this product is likely a result of non-specific enzymes known as amidases that can regenerate the carboxylic acid and can cause side effects resulting from COX inhibition. The metabolism of the amide to the carboxylic acid has been previously reported by Piazza et al, "A novel sulindac derivative that does not inhibit cyclooxygenases but potently inhibits tumor cell growth and induces apoptosis with antitumor activity" Cancer Prev. Res. 2: 574-580, 2009.

Notwithstanding the advances in treatments for cancer and other diseases there still remains an unmet medical need for improved drugs that are effective for the prevention and treatment of cancer, while at the same time exhibiting reduced adverse side effects.

SUMMARY

The present disclosure relates to compounds represented by the formula:

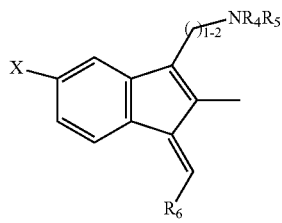

wherein each of $R_4$ and $R_5$ is selected from the group consisting of H, alkyl, a substituted or unsubstituted 5 or 6 member ring, provided that at least one of $R_4$ and $R_5$ is other than H; and when both $R_4$ and $R_5$ are a substituted or unsubstituted 5 or 6 member ring, both of $R_4$ and $R_5$ are a substituted or unsubstituted pyridyl ring;

$R_6$ is a substituted or unsubstituted 5 or 6 member ring; and X is a halogen; and pharmaceutically acceptable salts thereof, prodrugs thereof, solvates thereof and mixtures thereof.

The substituted or unsubstituted 5 or 6 member ring group for $R_4$, $R_5$ and $R_6$ can be a saturated or unsaturated ring and includes carbon, and optionally a heteroatom such as N or O.

The present disclosure is also concerned with a compound being represented by the following formula:

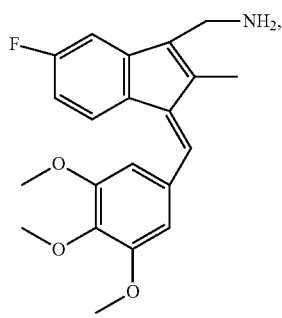 [SMILES: COc1cc(/C=C2/C(C)=C(CN)c3cc(F)ccc32)cc(OC)c1OC]

pharmaceutically acceptable salts thereof, prodrugs thereof, solvates thereof and mixtures thereof.

Another aspect of the present disclosure relates to pharmaceutical compositions containing a compound represented by the formula:

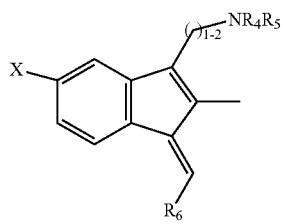

wherein each of $R_4$ and $R_5$ is selected from the group consisting of H, alkyl, a substituted or unsubstituted 5 or 6 member ring; and when both $R_4$ and $R_5$ are a substituted or unsubstituted 5 or 6 member ring, both of $R_4$ and $R_5$ are a substituted or unsubstituted pyridyl ring;

$R_6$ is a substituted or unsubstituted 5 or 6 member ring; and X is a halogen; and pharmaceutically acceptable salts thereof, prodrugs thereof, solvates thereof and mixtures thereof.

Also disclosed are methods of using the compounds of the present disclosure represented by the formula:

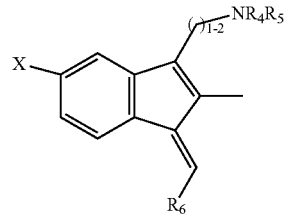

wherein each of $R_4$ and $R_5$ is selected from the group consisting of H, alkyl, a substituted or unsubstituted 5 or 6 member ring; and when both $R_4$ and $R_5$ are a substituted or unsubstituted 5 or 6 member ring, both of $R_4$ and $R_5$ are a substituted or unsubstituted pyridyl ring;

$R_6$ is a substituted or unsubstituted 5 or 6 member ring; and X is a halogen; and pharmaceutically acceptable salts thereof, prodrugs thereof, solvates thereof and mixtures thereof, in treating or preventing cancer in a mammal.

Another aspect of this disclosure is concerned with methods of using the compounds represented by the formula:

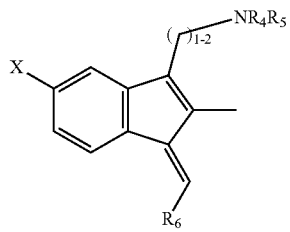

wherein each of $R_4$ and $R_5$ is selected from the group consisting of H, alkyl, a substituted or unsubstituted 5 or 6 member ring, provided that at least one of $R_4$ and $R_5$ is other than H; and when both $R_4$ and $R_5$ are a substituted or unsubstituted 5 or 6 member ring, both of $R_4$ and $R_5$ are a substituted or unsubstituted pyridyl ring;

$R_6$ is a substituted or unsubstituted 5 or 6 member ring; and X is a halogen; and pharmaceutically acceptable salts thereof, prodrugs thereof, solvates thereof and mixtures thereof, in treating chronic inflammatory diseases such as inflammatory bowel disease and certain neurodegenerative diseases including Alzheimer's disease.

A unique characteristic of the disclosed derivatives of sulindac is that they lack inhibitory effects on cyclooxygenase, types 1 and 2, enzymes, that otherwise would result in the depletion of physiologically important prostaglandins, which can result in gastrointestinal, renal and cardiovascular toxicity.

Another aspect is that the disclosed derivatives of sulindac were found to display potent tumor cell growth inhibitory activity against a variety of tumor cells types derived from solid tumors and hematological malignancies.

A still further aspect of this disclosure concerned with a method for preparing the above-disclosed compounds.

Certain compounds according to the present invention can be prepared by converting an ester of sulindac or a derivative therefore represented by the following formula:

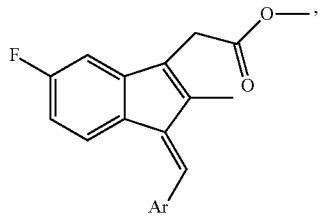

Ar is a substituted or unsubstituted 5 or 6 member ring. Non-limiting examples of Ar include

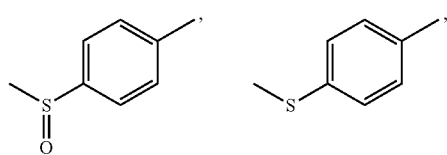

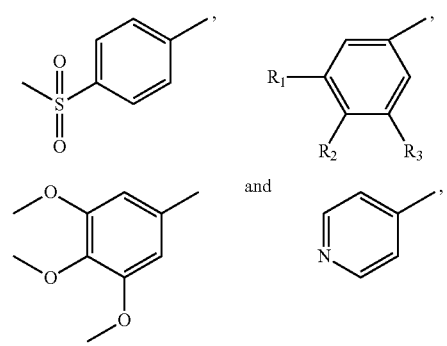

wherein each $R_1$, $R_2$ and $R_3$ is individually selected from the group consisting of H, Salkyl, alkyl and alkoxy;

An aldehyde represented by the following formula is obtained according to the above process step;

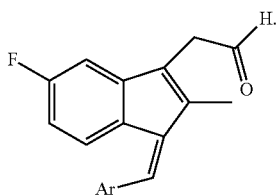

The aldehyde is the reacted with ammonia or an amine represented by $R_4R_5NH$. Each $R_4$ and $R_5$ is individually selected from the group consisting of H, alkyl, a substituted or unsubstituted 5 or 6 member ring; and when both $R_4$ and $R_5$ are a substituted or unsubstituted 5 or 6 member ring, both of $R_4$ and $R_5$ are a substituted or unsubstituted pyridyl ring. Non-limiting examples of $R_4$ and $R_5$ include

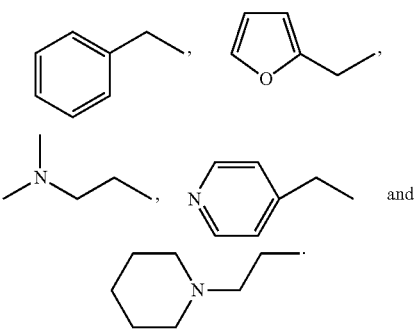

A compound represented by the formula is obtained by the above process step:

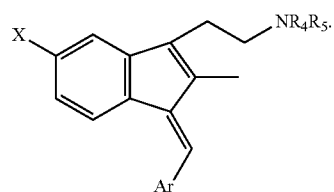

Other compounds according to the present disclosure can be prepared by the following scheme:

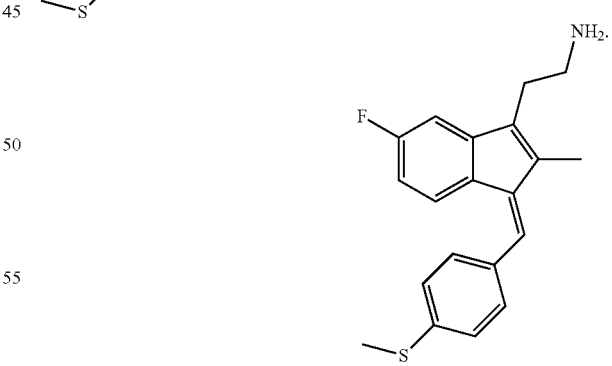

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive,

BRIEF DESCRIPTION OF FIGURES

FIG. 1 illustrates the cyclooxygenase (COX)-1 and -2 inhibitory activity of the NSAID, sulindac sulfide (SS), and the lack of this effect from (Z)—N-benzyl-2-(5-fluoro-2-methyl-1-(4-(methylsulfinyl)benzylidene)-1H-inden-3-yl)ethanamine (Compound 6 disclosed herein below), an amino derivative of sulindac.

FIG. 2 illustrates tumor cell growth inhibitory activity of a trimethoxy amino derivative of sulindac (Compound 6) and sulindac sulfide (SS) against the human MDA-MB-231 breast tumor cell line.

BEST AND VARIOUS MODES

The present disclosure is concerned with novel derivatives of sulindac represented by the formula:

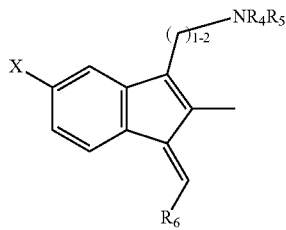

wherein each of $R_4$ and $R_5$ is selected from the group consisting of H, alkyl, a substituted or unsubstituted 5 or 6 member ring provided that at least one of $R_4$ and $R_5$ is other than H; and when both $R_4$ and $R_5$ are a substituted or unsubstituted 5 or 6 member ring, both of $R_4$ and $R_5$ are a substituted or unsubstituted pyridyl ring;

$R_6$ is a substituted or unsubstituted 5 or 6 member ring; and X is a halogen; and pharmaceutically acceptable salts thereof, prodrugs thereof, solvates thereof and mixtures thereof.

The substituted or unsubstituted 5 or 6 member ring group for $R_4$, $R_5$ and $R_6$ can be a saturated or unsaturated ring and includes carbon, and optionally a heteroatom such as N or O; substitutions include at least one alkyl group, halo group, alkoxy group, amino group or aminoalkyl group;

The alkyl group typically contains 1-12 carbon atoms. The alkyl group more typically contains 1-4 carbon atoms. Examples of suitable alkyl groups include methyl, ethyl and propyl. Examples branched alkyl groups include isopropyl and t-butyl. Examples of alkyl substituted aromatic groups (aralkyl) are phenyl $C_{1-3}$ alkyl and benzyl.

Typical alkyl substituted aromatic groups containing 7 to 10 carbon atoms in the aromatic ring. When substituted the alkyl group typically contains 1-6 carbon atoms.

Examples of halo groups are Cl, F, Br and I.

The term "aryl" refers to monocyclic or bicyclic aromatic hydrocarbon groups having 6 to 12 carbon atoms in the ring portion, such as phenyl, naphthyl, biphenyl, and diphenyl groups, each of which may be substituted such as with a halo or alkyl group.

Examples of 5 and 6 member ring groups are phenyl; N-heterocyclo groups such as pyridyl, pyrrolidinyl, piperidinyl, piperazinyl, pyridinyl, pyrrolyl, pyrazolyl, pyrazinyl pyrimidinyl, pyridazinyl, imidazoyl and imidazolidinyl; O-heterocyclo groups such as furanyl and pyranyl; heterocyclo groups containing both N and O such as morpholinyl. When substituted these groups are typically substituted with at least one alkyl group, halo, alkoxy group, amino group or aminoalkyl group. The rings can be substituted with more than one substituent, for instance, trimethoxy.

It is of course understood that the compounds of the present disclosure relate to all optical isomers and stereo-isomers at the various possible atoms of the molecule, unless specified otherwise.

The compounds according to this disclosure may form prodrugs at hydroxyl or amino functionalities using alkoxy, amino acids, etc. groups as the prodrug forming moieties. For instance, the hydroxymethyl position may form mono-, di- or triphosphates and again these phosphates can form prodrugs.

Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the disclosure.

"Pharmaceutically acceptable salts" refer to derivatives of the disclosed compounds wherein the parent compound is modified by making acid or base salts thereof. The compounds of this disclosure form acid addition salts with a wide variety of organic and inorganic acids and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

"Solvates" refers to the compound formed by the interaction of a solvent and a solute and includes hydrates. Solvates are usually crystalline solid adducts containing solvent molecules within the crystal structure, in either stoichiometric or nonstoichiometric proportions.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

The term "precancerous condition" refers to patients having a propensity for being afflicted with cancer.

Compounds according to the present disclosure can, for example, be prepared by the following methods.

Some exemplary compounds were prepared by the following scheme.

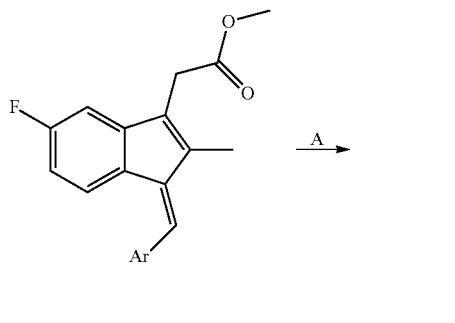

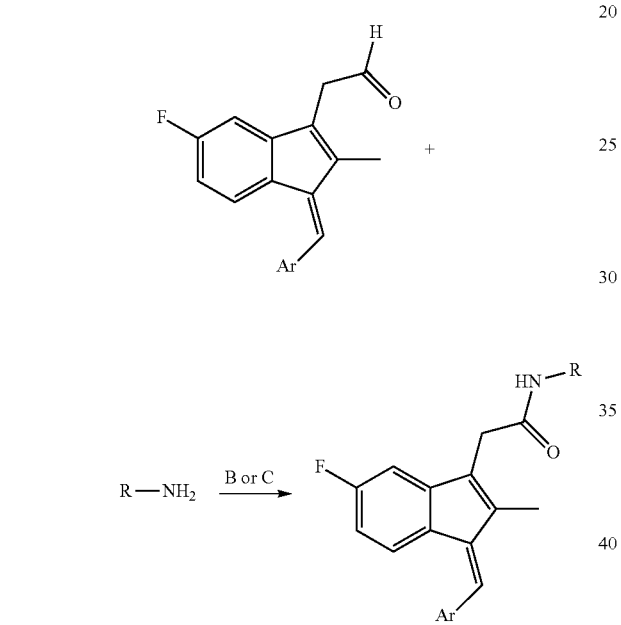

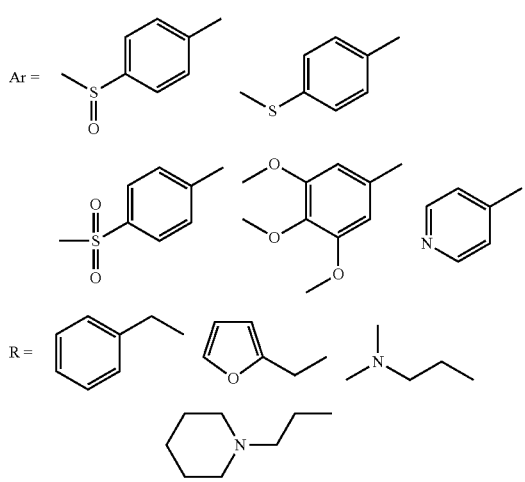

A) DIBALH, Toluene, -70° C. B) NaBH$_4$, MeOH, rt C) Sodium triacetoxyborohydride, 1,2-Dichloroethane, rt

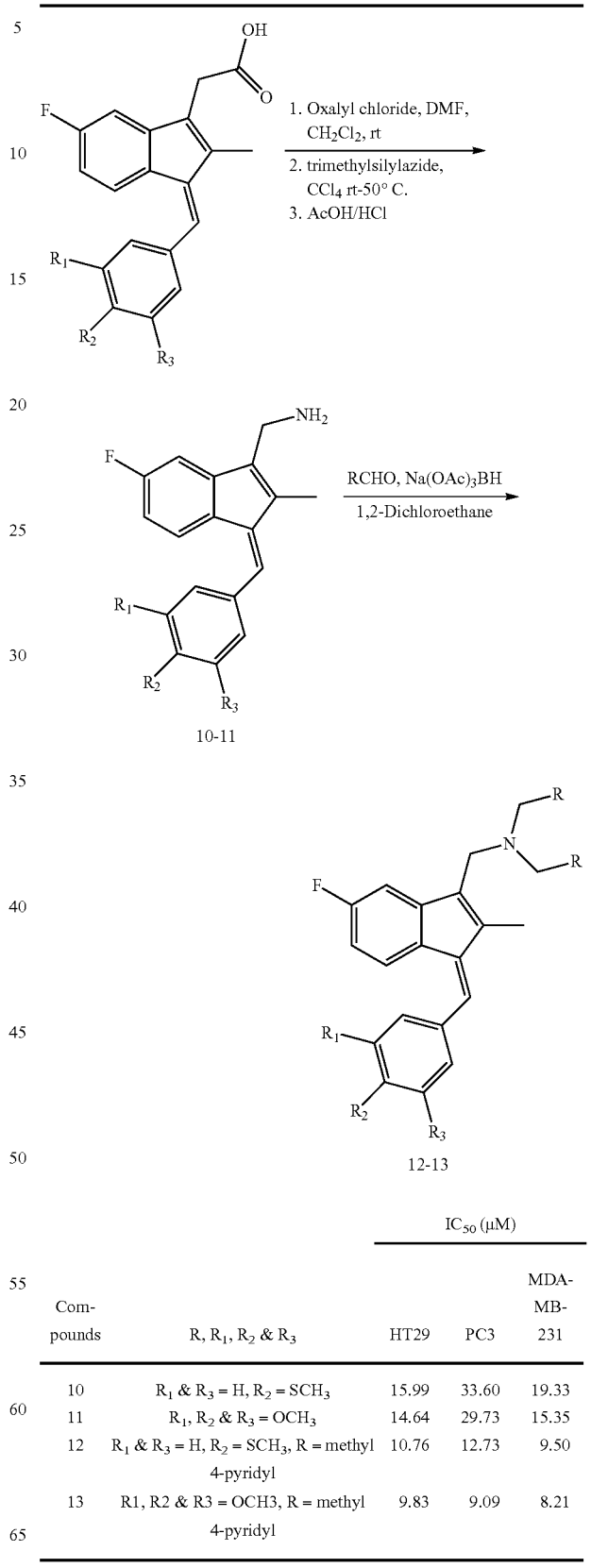

| Compounds | R, R$_1$, R$_2$ & R$_3$ | IC$_{50}$ (µM) | | |
|---|---|---|---|---|
| | | HT29 | PC3 | MDA-MB-231 |
| 10 | R$_1$ & R$_3$ = H, R$_2$ = SCH$_3$ | 15.99 | 33.60 | 19.33 |
| 11 | R$_1$, R$_2$ & R$_3$ = OCH$_3$ | 14.64 | 29.73 | 15.35 |
| 12 | R$_1$ & R$_3$ = H, R$_2$ = SCH$_3$, R = methyl 4-pyridyl | 10.76 | 12.73 | 9.50 |
| 13 | R1, R2 & R3 = OCH3, R = methyl 4-pyridyl | 9.83 | 9.09 | 8.21 |

Also various compounds according to the present disclosure can be prepared as follows:

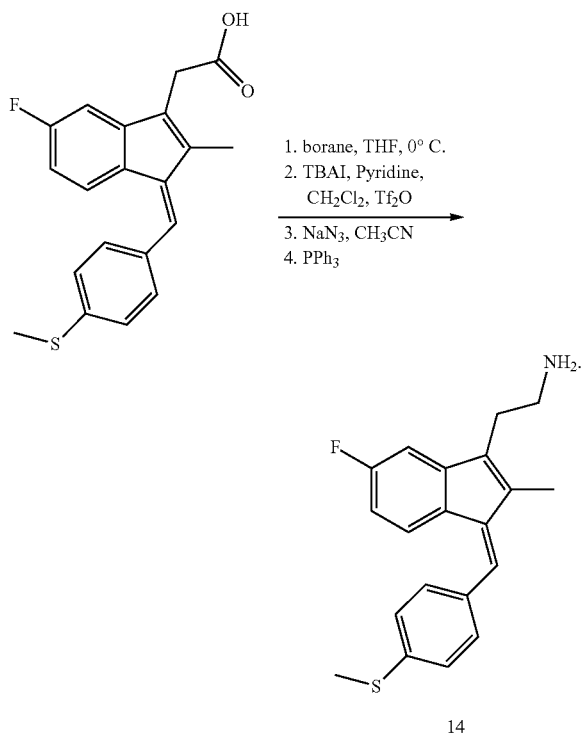

14

PPh$_3$ refers to triphenylphosphine and Tf$_2$O refers trifluoromethanesulfonic acid anhydride Method A To a solution of ester (1 equivalent) in dry toluene at −70° C. under argon atmosphere was slowly added diisobutyl aluminium hydride (1 M) in toluene (1.2 equivalent) and the resulting mixture stirred at −70° C. for 1-2 hours. Methanol (10 mL) was added slowly at −70° C. and allowed to warm to room temperature. The reaction mixture was washed with 1N aqueous HCl and extracted with CH$_2$Cl$_2$ (2×20 mL), The combined organic fractions were dried over anhydrous Na$_2$SO$_4$ and evaporated in vacuuo. The crude aldehyde was used for the next step without further purification.

Method B

Aldehyde (1 equivalent) and amine (1.5 equivalent) were mixed in dry MeOH at room temperature under argon atmosphere. The reaction mixture was stirred at room temperature and progress of the reaction was monitored by TLC. After the complete formation of aldimine (3-5 h), NaBH$_4$ (1.5 equivalent) was added slowly at room temperature. The reaction mixture was stirred for 15 minutes and quenched with 1N NaOH. The product was extracted with CH$_2$Cl$_2$ (3×20 mL) and dried over anhydrous Na$_2$SO$_4$. The solvent was evaporated in vacuuo and purified by column chromatography to afford sulindac amine as yellow viscous liquid.

Method C

Aldehyde (1 equivalent) and amine (1.5 equivalent) were mixed in dry 1,2-dichloroethane under argon atmosphere and then treated with sodium triacetoxyborohydride (1.5 equivalent). The reaction mixture was stirred at room temperature until the complete disappearance of aldehyde (3-5 h). The reaction mixture was quenched with aqueous saturated NaHCO$_3$ and the product was extracted with CH$_2$Cl$_2$ (3×20 mL). The combined organic fractions were dried over anhydrous Na$_2$SO$_4$ and evaporated in vacuuo. The product was purified by column chromatography to afford sulindac amine as yellow viscous liquid. Typical yields of the reactions in Method B & C is range from 50 to 90%.

Method D

Oxalyl chloride was added to a solution of sulindac (1.0 equivalent) in CH$_2$Cl$_2$ (50 mL) followed by 2 drops of DMF. The resulted reaction mixture was stirred at room temperature for 1 h. Solvent was removed in vacuuo and the crude acid chloride was used in the next step without any further purification. Crude acid chloride was suspended in CCl$_4$ (25 mL) and was added trimethylsilyl azide (1.5 equivalent) at room temperature. The reaction mixture was stirred at room temperature 15 min. and slowly heated while stirring until the evolution of nitrogen ceased. Solvent was removed under reduced pressure to give isocyanate as viscous yellow liquid. To the crude isocyanate in acetic acid (80 mL) was added Conc. HCl (20 mL). The reaction mixture was heated on a steam bath at 50° C. for 30 min. Diluted the reaction mixture with cold H$_2$O (100 mL) and filtered. The solid filtered was washed with water and then ether to form sulindac methaneamine as hydrochloride salt.

Method E

Aldehyde (2.0 equivalent) and amine (1.0 equivalent) were mixed in dry 1,2-dichloroethane under argon atmosphere and then treated with sodium triacetoxyborohydride (1.5 equivalent). The reaction mixture was stirred at room temperature until the complete disappearance of amine (3-5 h). The reaction mixture was quenched with aqueous saturated NaHCO$_3$ and the product was extracted with CH$_2$Cl$_2$ (3×20 mL). The combined organic fractions were dried over anhydrous Na$_2$SO$_4$ and evaporated in vacuuo. The product was purified by using Isco Teledyne chromatographic machine to afford sulindac amine as yellow viscous liquid.

Method F

To a solution of sulindac sulfide (1 equivalent) in THF at 0° C. under nitrogen atmosphere, was added a solution of borane in THF (1.2 equivalent) and the reaction mixture stirred in the cold for 30 minutes, then at room temperature for 2 h. Water was slowly added to the reaction mixture and extracted with CH$_2$Cl$_2$ (3×20 mL). The crude alcohol was purified by column chromatography. To a solution of above alcohol and tetrabutylammonium iodide (2 equivalent) in pyridine (2.2 equivalent) and CH$_2$Cl$_2$ was slowly added trifluoromethane sulfonic anhydride (1.8 equivalent) at −78° C. for 15 minutes, then at room temperature for 1 h. It was then diluted with CH$_2$Cl$_2$ (50 mL) and washed successively with 10% aqueous sodium thiosulfate, 1N aqueous HCl, saturated NaHCO$_3$, and brine. The crude residue from the evaporation of the organic phase was chromatgraphed to obtain sulindac iodide. The above iodide compound was refluxed with sodium azide (1.5 equivalent) in CH$_3$CN for 10 h. Triphenyl phosphine (PPh$_3$) (1 equivalent) was added to above solution at room temperature and the reaction mixture was stirred under nitrogen atmosphere for 3 hours. CH$_2$Cl$_2$ (50 mL) was added to the reaction mixture and washed with saturated NaHCO$_3$. Solvent was removed under reduced pressure and the product was purified by silica gel column chromatography to provide sulindac amine as yellow viscous liquid.

Example 1

(Z)—N-benzyl-2-(5-fluoro-2-methyl-1-(4-(methylsulfinyl)benzylidene)-1H-inden-3-yl)ethanamine (1)

By following methods A & C, the title compound 1 was obtained as a yellow viscous liquid.

$^1$H NMR (CDCl$_3$, 300 MHz): δ7.72-7.63 (4H, in, 2'-H, 3'-H, 5'-H, 6'-H), 7.32-7.22 (5H, m, Ph-H), 7.15 (1H, dd, J=5.4 Hz, 8.4 Hz, 7-H), 7.08 (1H, s, 8-H), 6.85 (1H, dd, J=2.7 Hz, 9.3 Hz, 4-H), 6.57 (1H, ddd, J=2.4 Hz, 9.3 Hz, 11.1 Hz, 6-H), 3.84 (2H, s, —CH$_2$-Ph), 2.90-2.75 (4H, m, —CH$_2$—CH$_2$—NH), 2.80 (3H, s, —SOCH$_3$), 2.17 (3H, s, 2-CH$_3$). HRMS calcd for [C$_{27}$H$_{26}$FNOS+H]$^+$: 432.17919. Found: 432.17990. Anal. calcd for [C$_{27}$H$_{26}$FNOS+0.5H$_2$O]: C, 73.61; H, 6.18; N, 3.18. Found: C, 73.74; H, 5.95; N, 3.08.

Example 2

(Z)-2-(5-fluoro-2-methyl-1-(4-(methylsulfinyl)benzylidene)-1H-inden-3-yl)-N-(furan-2-ylmethyl)ethanamine (2)

By following methods A & B, the title compound 2 was obtained as a yellow viscous liquid.

ESI-MS m/z: 422 [M+H]$^+$. $^1$H NMR (CDCl$_3$, 300 MHz): δ 7.72-7.64 (4H, m, 2'-H, 3'-H, 5'-H, 6'-H), 7.35 (1H, dd, J=0.6 Hz, 1.8 Hz, 5"-H), 7.14 (1H, dd, J=5.1 Hz, 8.1 Hz, 7-H), 7.08 (1H, s, 8-H), 6.85 (1H, dd, J=2.4 Hz, 9.0 Hz, 4-H), 6.57 (1H, ddd, J=2.4 Hz, 9.0 Hz, 10.8 Hz, 6-H), 6.31 (1H, dd, J=2.1 Hz, 3.3 Hz, 4"-H), 6.17 (1H, dd, J=0.6 Hz, 3.0 Hz, 3"-H), 3.83 (2H, s, —CH$_2$-Furan), 2.84-2.76 (4H, m, —CH$_2$—CH$_2$—NH), 2.80 (3H, s, —SOCH$_3$), 2.16 (3H, s, 2-CH$_3$). Anal. calcd for [C$_{25}$H$_{24}$FNO$_2$S+0.4H$_2$O]: C, 70.04; H, 5.83; N, 3.27. Found: C, 70.05; H, 5.95; N, 3.26.

Example 3

(Z)—N-benzyl-2-(5-fluoro-2-methyl-1-(4-(methylthio)benzylidene)-1H-inden-3-yl)ethanamine (3)

By following methods A & B, the title compound 3 was obtained as a yellow viscous liquid.

ESI-MS m/z: 416 [M+H]$^+$. $^1$H NMR (CDCl$_3$, 300 MHz): δ 7.44 (2H, d, J=8.1 Hz, 3'-H, 5'-H), 7.35-7.21 (8H, m, 2'-H, 6'-H, 7-H, Ph-H), 7.06 (1H, s, 8-H), 6.84 (1H, dd, J=2.4 Hz, 9.0 Hz, 4-H), 6.59 (1H, ddd, J=2.4 Hz, 9.3 Hz, 10.8 Hz, 6-H), 3.83 (2H, s, —CH$_2$-Ph), 2.89-2.75 (4H, m, —CH$_2$—CH$_2$—NH), 2.54 (3H, s, —SCH$_3$), 2.16 (3H, s, 2-CH$_3$). HRMS calcd for [C$_{27}$H$_{26}$FNS+H]$^+$: 416.18428. Found: 416.18452. Anal. calcd for [C$_{27}$H$_{26}$FNS+0.2H$_2$O]: C, 77.36; H, 6.35; N, 3.34. Found: C, 77.40; H, 6.48; N, 3.21.

Example 4

(Z)-2-(5-fluoro-2-methyl-1-(4-(methylthio)benzylidene)-1H-inden-3-yl)-N-(furan-2-ylmethyl)ethanamine (4)

By following methods A & B, the title compound 4 was obtained as a yellow viscous liquid.

ESI-MS m/z: 406 [M+H]$^+$. $^1$H NMR (CDCl$_3$, 300 MHz): δ 7.44 (2H, d, J=8.4 Hz, 3'-H, 5'-H), 7.36-7.26 (4H, m, 2'-H, 6'-H, 7-H, 5"-H), 7.06 (1H, s, 8-H), 6.84 (1H, dd, J=2.4 Hz, 9.0 Hz, 4-H), 6.59 (1H, ddd, J=2.4 Hz, 9.3 Hz, 10.8 Hz, 6-H), 6.31 (1H, dd, J=1.8 Hz, 3.3 Hz, 4"-H), 6.16 (1H, dd, J=0.6 Hz, 3.0 Hz, 3"-H), 3.82 (2H, s, —CH$_2$-Furan), 2.86-2.73 (4H, m, —CH$_2$—CH$_2$—NH), 2.54 (3H, s, —SCH$_3$), 2.16 (3H, s, 2-CH$_3$). HRMS calcd for [C$_{25}$H$_{24}$FNOS+H]$^+$: 406.16354. Found: 406.16388. Anal. calcd for [C$_{25}$H$_{24}$FNOS+0.2H$_2$O]: C, 73.39; H, 6.01; N, 3.42. Found: C, 73.25; H, 5.97; N, 3.20.

Example 5

(Z)-2-(5-fluoro-2-methyl-1-(4-(methylthio)benzylidene)-1H-inden-3-yl)-N-(2-(piperidin-1-yl)ethyl)ethanamine (5)

By following methods A & B, the title compound 5 was obtained as a yellow viscous liquid.

ESI-MS m/z: 437 [M+H]$^+$. $^1$H NMR (CDCl$_3$, 300 MHz): δ 7.43 (2H, d, J=8.4 Hz, 3'-H, 5'-H), 7.36 (1H, dd, J=5.4 Hz, 8.4 Hz, 7-H), 7.29 (2H, d, J=8.4 Hz, 2'-H, 6'-H), 7.09 (1H, s, 8-H), 6.87 (1H, dd, J=2.4 Hz, 9.0 Hz, 4-H), 6.60 (1H, ddd, J=2.4 Hz, 9.0 Hz, 11.7 Hz, 6-H), 2.88-2.77 (6H, m, —CH$_2$—CH$_2$—NH—CH$_2$—), 2.54 (3H, s, —SCH$_3$), 2.51 (2H, t, J=6.0 Hz, CH$_2$—NO, 2.38 (4H, t, J=5.1 Hz, 2"-H, 6"-H), 2.19 (3H, s, 2-CH$_3$), 1.51-1.48 (4H, m, 3"-H, 5"-H), 1.41-1.35 (2H, m, 4"-H). Anal. calcd for [C$_{27}$H$_{33}$FN$_2$S+0.8H$_2$O]: C, 71.90; H, 7.73; N, 6.21. Found: C, 72.04; H, 8.08; N, 5.81.

Example 6

(Z)—N-1-(2-(5-fluoro-2-methyl-1-(4-(methylthio)benzylidene)-1H-inden-3-yl)ethyl)-N2,N2-dimethylethane-1,2-diamine (6)

By following methods A & B, the title compound 6 was obtained as a yellow viscous liquid.

ESI-MS m/z: 397 [M+H]$^+$. $^1$H NMR (CDCl$_3$, 300 MHz): δ 7.44 (2H, d, J=8.1 Hz, 3'-H, 5'-H), 7.35 (1H, dd, J=5.1 Hz, 8.4 Hz, 7-H), 7.29 (2H, d, J=8.4 Hz, 2'-H, 6'-H), 7.07 (1H, s, 8-H), 6.88 (1H, dd, J=2.4 Hz, 9.3 Hz, 4-H), 6.59 (1H, ddd, J=2.4 Hz, 9.3 Hz, 11.1 Hz, 6-H), 2.86-2.72 (6H, m, —CH$_2$—CH$_2$—NH—CH$_2$—), 2.54 (3H, s, —SCH$_3$), 2.45 (2H, t, J=6.3 Hz, CH$_2$—NO, 2.22 (6H, s, —N(CH$_3$)$_2$), 2.17 (3H, s, 2-CH$_3$). HRMS calcd for [C$_{24}$H$_{29}$FN$_2$S+H]$^+$: 397.21082. Found: 397.21066.

Example 7

(Z)—N-benzyl-2-(5-fluoro-2-methyl-1-(4-(methylsulfonyl)benzylidene)-1H-inden-3-yl)ethanamine (7)

By following methods A & C, the title compound 7 was obtained as a yellow viscous liquid.

$^1$H NMR (CDCl$_3$, 300 MHz): δ 8.00 (2H, d, J=8.4 Hz, 3'-H, 5'-H), 7.69 (2H, d, J=8.4 Hz, 2'-H, 6'-H), 7.32-7.22 (5H, m, Ph-H), 7.09 (1H, dd, J=5.2 Hz, 8.4 Hz, 7-H), 7.04 (1H, s, 8-H), 6.84 (1H, dd, J=2.4 Hz, 8.8 Hz, 4-H), 6.57 (1H, ddd, J=2.4 Hz, 8.8 Hz, 11.2 Hz, 6-H), 3.84 (2H, s, —CH$_2$-Ph), 3.13

(3H, s, —SO$_2$CH$_3$), 2.89 (2H, t, J=6.8 Hz, —CH$_2$—CH$_2$—NH), 2.79 (2H, t, J=6.4 Hz, —CH$_2$—CH$_2$—NH), 2.16 (3H, s, 2-CH$_3$). HRMS calcd for [C$_{27}$H$_{26}$FNO$_2$S+H]$^+$: 448.17410. Found: 448.17467. Anal. calcd for [C$_{27}$H$_{26}$FNO$_2$S+0.5H$_2$O]: C, 71.03; H, 5.96; N, 3.07. Found: C, 70.82; H, 5.71; N, 2.93.

Example 8

(Z)—N-benzyl-2-(5-fluoro-2-methyl-1-(3,4,5-trimethoxybenzylidene)-1H-inden-3-yl)ethanamine (8)

By following methods A & C, the title compound 8 was obtained as a yellow viscous liquid (LCMS purity: 100%).
$^1$H NMR (CDCl$_3$, 300 MHz): δ 7.41 (1H, dd, J=5.2 Hz, 8.4 Hz, 7-H), 7.32-7.22 (5H, m, Ph-H), 7.07 (1H, s, 8-H), 6.86 (1H, dd, J=2.4 Hz, 9.2 Hz, 4-H), 6.73 (2H, s, 2'-H, 6'-H), 6.60 (1H, ddd, J=2.4 Hz, 9.2 Hz, 11.6 Hz, 6-H), 3.92 (3H, s, 4'-OCH$_3$), 3.87 (2H, s, —CH$_2$-Ph), 3.84 (6H, s, 3'-OCH$_3$, 5'-OCH$_3$), 2.89 (2H, t, J=6.8 Hz, —CH$_2$—CH$_2$—NH), 2.80 (2H, t, J=6.8 Hz, —CH$_2$—CH$_2$—NH), 2.16 (3H, s, 2-CH$_3$). HRMS calcd for [C$_{29}$H$_{30}$FNO$_3$+H]$^+$: 460.22825. Found: 460.22836.

Example 9

(Z)—N-benzyl-2-(5-fluoro-2-methyl-1-(pyridin-4-ylmethylene)-1H-inden-3-yl)ethanamine (9)

By following methods A & B, the title compound 9 was obtained as a yellow viscous liquid.
ESI-MS, m/z: 371 [M+H]$^+$. $^1$H NMR (CDCl$_3$, 300 MHz): δ 8.68 (2H, d, J=5.7 Hz, 3'-H, 5'-H), 7.38 (2H, d, J=5.4 Hz, 2'-H, 6'-H), 7.33-7.21 (5H, m, Ph-H), 7.11 (1H, dd, J=5.1 Hz, 8.4 Hz, 7-H), 6.95 (1H, s, 8-H), 6.85 (1H, dd, J=2.4 Hz, 9.0 Hz, 4-H), 6.57 (1H, ddd, J=2.4 Hz, 9.0 Hz, 11.4 Hz, 6-H), 3.87 (2H, s, —CH$_2$-Ph), 2.89-2.79 (4H, m, —CH$_2$—CH$_2$—NH), 2.15 (3H, s, 2-CH$_3$). Anal, calcd for [C$_{25}$H$_{23}$FN$_2$+0.5H$_2$O]: C, 75.89; H, 6.57; N, 7.08. Found: C, 75.87; H, 5.87; N, 6.25.

Example 10

(Z)-(5-Fluoro-2-methyl-1-(4-(methylthio)benzylidene)-1H-inden-3-yl)methanamine (10)

By following method D, the title compound 10 was obtained as a yellow viscous liquid in 70% (HPLC purity: 98.7%) yield.
$^1$H NMR (DMSO, 400 MHz): δ 7.48 (2H, d, J=8.4 Hz, 2'-H, 6'-H), 7.35 (2H, d, J=8.4 Hz, 3'-H, 5'-H), 7.32 (1H, dd, J=5.6 Hz, 8.4 Hz, 7-H), 7.24 (1H, s, 10-H), 7.20 (1H, dd, J=2.0 Hz, 9.2 Hz, 4-H), 6.71 (1H, td, J=2.0 Hz, 9.2 Hz, 6-H), 3.65 (2H, s, CH$_2$—NH$_2$), 2.53 (3H, s, —SCH$_3$), 2.15 (3H, s, 2-CH$_3$), 1.64 (2H, s, NH$_2$).

Example 11

(Z)-(5-Fluoro-2-methyl-1-(3,4,5-trimethoxybenzylidene)-1H-inden-3-yl)methanamine (12)

By following method D, the title compound 11 was obtained as a yellow solid in 88% (HPLC purity: 90.5%) yield.
M. P. 108.8° C.
$^1$H NMR (CDCl$_3$, 400 MHz): δ 7.45 (1H, dd, J=4.8 Hz, 8.0 Hz, 7-H), 7.14 (1H, s, 10-H), 6.96 (1H, dd, J=2.4 Hz, 8.4 Hz, 4-H), 6.74 (2H, s, 2'-H, 6'-H), 6.61 (1H, td, J=2.8 Hz, 9.6 Hz, 6-H), 3.93 (3H, s, 4'-OCH$_3$), 3.84 (6H, s, 3'-OCH$_3$, 5'-OCH$_3$), 3.82 (2H, s, CH$_2$—NH$_2$), 2.73 (2H, s, NH$_2$), 2.21 (3H, s, 2-CH$_3$).

Example 12

(Z)-1-(5-Fluoro-2-methyl-1-(4-(methylthio)benzylidene)-1H-inden-3-yl)-N,N-bis(pyridin-4-ylmethyl)methanamine (12)

By following methods D and E, the title compound 11 was obtained as a yellow viscous liquid in 84% (HPLC purity: 95.9%) yield.
$^1$H NMR (CDCl$_3$, 400 MHz): δ 8.56 (4H, dd, J=1.6 Hz, 4.8 Hz, 2''-H, 6''-H), 7.41 (2H, d, J=8.4 Hz, 2'-H, 6'-H), 7.32 (1H, dd, J=5.2 Hz, 8.4 Hz, 7-H), 7.28-7.26 (6H, m, 3'-H, 5'-H, 3''-H, 5''-H), 7.09 (1H, s, 10-H), 6.98 (1H, dd, J=2.4 Hz, 9.6 Hz, 4-H), 6.58 (1H, td, J=2.4 Hz, 9.2 Hz, 6-H), 3.55 (4H, s, CH$_2$—Ar), 3.51 (2H, s, 3-CH$_2$), 2.53 (3H, s, —SCH$_3$), 2.18 (3H, s, 2-CH$_3$). HRMS calcd for [C$_{31}$H$_{28}$FN$_3$S+H]$^+$: 494.20607. Found: 494.20636.

Example 13

(Z)-1-(5-Fluoro-2-methyl-1-(3,4,5-trimethoxybenzylidene)-1H-inden-3-yl)-N,N-bis(pyridin-4-ylmethyl)methanamine (13)

By following methods D and E, the title compound 13 was obtained as a yellow solid in 75% (HPLC purity: 100%) yield.
M. P. 66.4° C.
$^1$H NMR (CDCl$_3$, 400 MHz): δ 8.56 (4H, dd, J=1.6 Hz, 4.4 Hz, 2''-H, 6''-H), 7.39 (1H, dd, J=5.2 Hz, 8.4 Hz, 7-H), 7.28 (4H, dd, J=1.6 Hz, 4.8 Hz, 3''-H, 5''-H), 7.09 (1H, s, 10-H), 7.00 (1H, dd, J=2.0 Hz, 9.2 Hz, 4-H), 6.71 (2H, s, 2'-H, 6'-H), 6.60 (1H, td, J=2.4 Hz, 9.2 Hz, 6-H), 3.92 (3H, s, 4'-OCH$_3$), 3.83 (6H, s, 3'-OCH$_3$, 5'-OCH$_3$), 3.56 (4H, s, CH$_2$Ar), 3.51 (2H, s, 3-CH$_2$), 2.19 (3H, s, 2-CH$_3$). HRMS calcd for [C$_{33}$H$_{32}$FN$_3$O$_3$+H]$^+$: 538.25005. Found: 538.25017.

Example 14

(Z)-2-(5-Fluoro-2-methyl-1-(4-(methylthio)benzylidene)-1H-inden-3-yl)ethanamine

By following method F, the title compound 14 was obtained as a yellow viscous liquid.
ESI-MS m/z: 326.18 [M+H]$^+$. $^1$H NMR (CDCl$_3$, 300 MHz): δ 7.43 (2H, d, J=8.1 Hz, 3'-H, 5'-H), 7.34 (1H, dd, J=5.4 Hz, 8.4 Hz, 7-H), 7.28 (2H, d, J=8.1 Hz, 2'-H, 6'-H), 7.08 (1H, s, 10-H), 6.84 (1H, dd, J=2.4 Hz, 9.0 Hz, 4-H), 6.56 (1H, td, J=2.4 Hz, 9.0 Hz, 6-H), 2.94 (2H, t, J=6.3 Hz, CH$_2$—NH$_2$), 2.71 (2H, t, J=6.9 Hz, 3-CH$_2$), 2.54 (3H, s, —SCH$_3$), 2.18 (3H, s, 2-CH$_3$). HRMS calcd for [C$_{20}$H$_{20}$FNS+H]$^+$: 326.13732. Found: 326.13805.

It has been found according to the present disclosure that compounds disclosed are surprisingly and advantageously useful in treating mammalian cancer.

The following tables demonstrate improved properties achievable by the present invention.

TABLE 1

Colon tumor cell growth inhibitory activity of sulindac amine derivatives and reductive amination products.
Results from three human colon tumor cell lines are shown in the Tables shown below.

| Compound designation | Structure | Colon tumor cell growth inhibitory activity (IC$_{50}$, μM) | | |
|---|---|---|---|---|
| | | HT29 | SW480 | HCT116 |
| 1 | 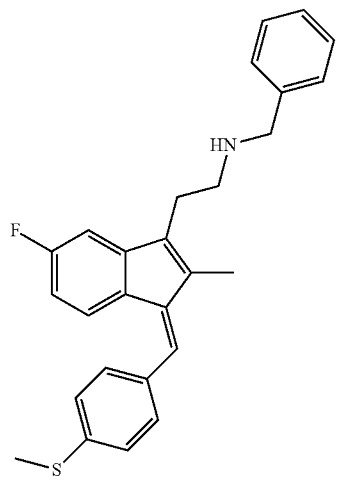 [SMILES: CSc1ccc(/C=C2/C(C)=C(CCNCc3ccccc3)c3cc(F)ccc32)cc1] | 2.7 | 3.3 | 4.9 |
| 2 | 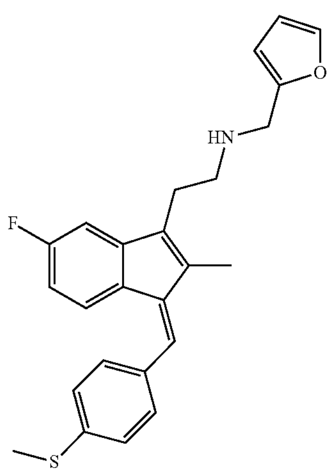 [SMILES: CSc1ccc(/C=C2/C(C)=C(CCNCc3ccco3)c3cc(F)ccc32)cc1] | 4.6 | 5.2 | 7.6 |
| 3 | 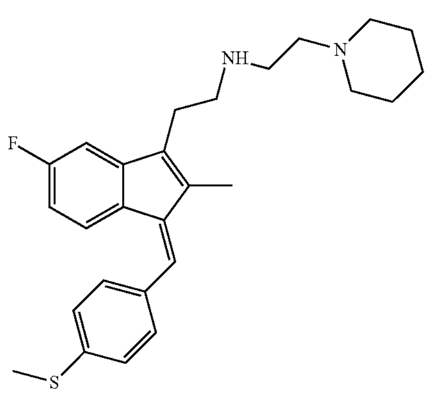 [SMILES: CSc1ccc(/C=C2/C(C)=C(CCNCCN3CCCCC3)c3cc(F)ccc32)cc1] | 3.0 | 5.4 | 3.8 |

TABLE 1-continued
Colon tumor cell growth inhibitory activity of sulindac amine derivatives and reductive amination products.
Results from three human colon tumor cell lines are shown in the Tables shown below.
| | | | | |
|---|---|---|---|---|
| 4 | 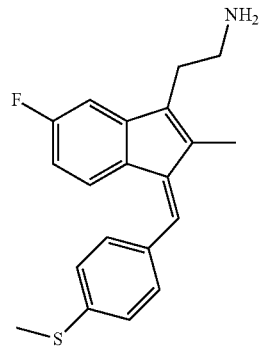 [SMILES: CSc1ccc(/C=C2/C(C)=C(CCN)c3cc(F)ccc32)cc1] | 4.1 | 4.1 | 4.9 |
| 5 | 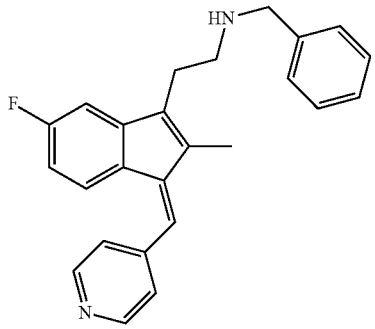 [SMILES: CC1=C(CCNCc2ccccc2)c2cc(F)ccc2/C1=C\c1ccncc1] | 2.7 | — | — |
| 6 | 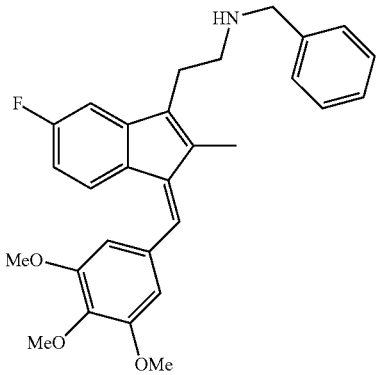 [SMILES: COc1cc(/C=C2/C(C)=C(CCNCc3ccccc3)c3cc(F)ccc32)cc(OC)c1OC] | 6.1 | 7.07 | 6.72 |
| 7 | 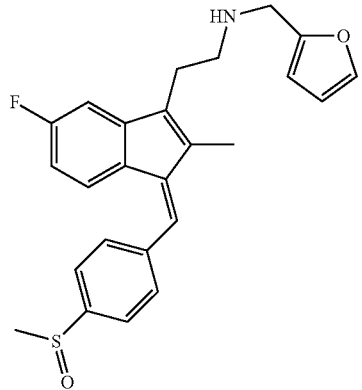 [SMILES: CC1=C(CCNCc2ccco2)c2cc(F)ccc2/C1=C\c1ccc(S(C)=O)cc1] | 2.3 | — | — |

TABLE 1-continued

Colon tumor cell growth inhibitory activity of sulindac amine derivatives and reductive amination products.
Results from three human colon tumor cell lines are shown in the Tables shown below.

| No | Structure | | |
|---|---|---|---|
| 8 | [structure: 5-fluoro-2-methyl-1-(4-methylsulfinylbenzylidene)-3-(2-(benzylamino)ethyl)-indene] | 1.3 | — — |
| 9 | [structure: 5-fluoro-2-methyl-1-(4-methylsulfonylbenzylidene)-3-(2-(benzylamino)ethyl)-indene] | 1.8 | — — |

| | | Tumor cell growth inhibitory activity (IC$_{50}$, μM) | | |
|---|---|---|---|---|
| No | Structure | HT29 | PC3 | MDA-MB-231 (breast) |
| 10 | [structure: 5-fluoro-2-methyl-1-(4-methylthiobenzylidene)-3-(aminomethyl)-indene]<br>Chemical Formula:<br>$C_{19}H_{18}FNS$ | 15.99 | 33.60 | 19.33 |

TABLE 1-continued

Colon tumor cell growth inhibitory activity of sulindac amine derivatives and reductive amination products.
Results from three human colon tumor cell lines are shown in the Tables shown below.

| 12 | 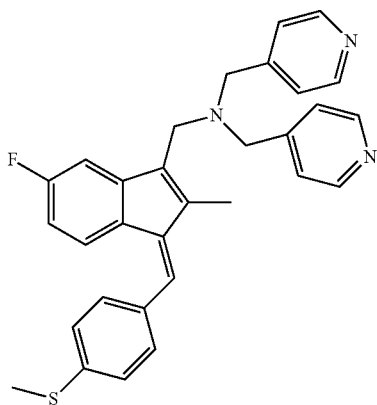 [SMILES: CSc1ccc(/C=C2/C(C)=C(CN(Cc3ccncc3)Cc3ccncc3)c3cc(F)ccc32)cc1]  Chemical Formula: $C_{31}H_{28}FN_3S$ | 10.76 | 12.73 | 9.50 |
| --- | --- | --- | --- | --- |
| 11 | 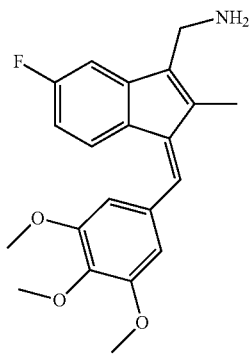  Chemical Formula: $C_{21}H_{22}FNO_3$ | 14.64 | 29.73 | 15.35 |
| 13 | 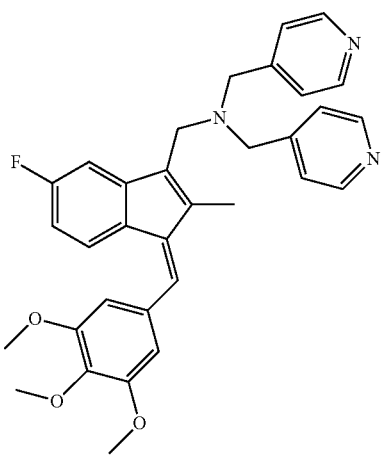 [SMILES: COc1cc(/C=C2/C(C)=C(CN(Cc3ccncc3)Cc3ccncc3)c3cc(F)ccc32)cc(OC)c1OC]  Chemical Formula: $C_{33}H_{32}FN_3O_3$ | 9.83 | 9.09 | 8.21 |

| Compound designation | Structure | Breast tumor cell growth inhibitory activity (IC$_{50}$, µM) | | |
| --- | --- | --- | --- | --- |
| | | MCF-7 | MDA-MB-231 | SKBR3 |

TABLE 1-continued
Colon tumor cell growth inhibitory activity of sulindac amine derivatives and reductive amination products.
Results from three human colon tumor cell lines are shown in the Tables shown below.
| | | | | |
|---|---|---|---|---|
| 1 | 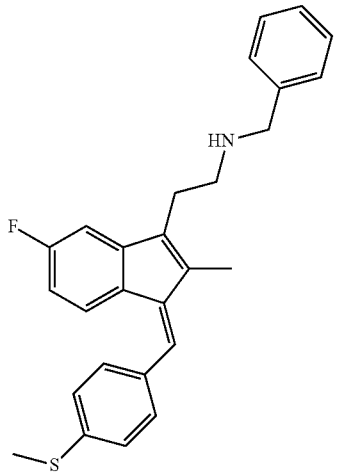 | 6.8 | 5.8 | 3.4 |
| 2 | 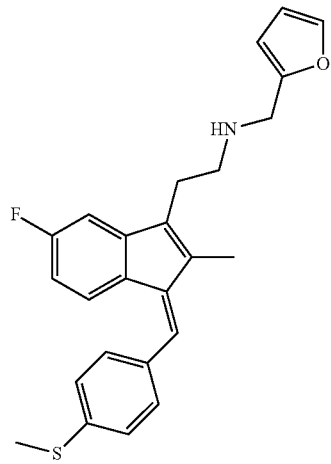 [SMILES: CSc1ccc(/C=C2/C(C)=C(CCNCc3ccco3)c3cc(F)ccc32)cc1] | 15.2 | 10.2 | 6.4 |
| 3 | 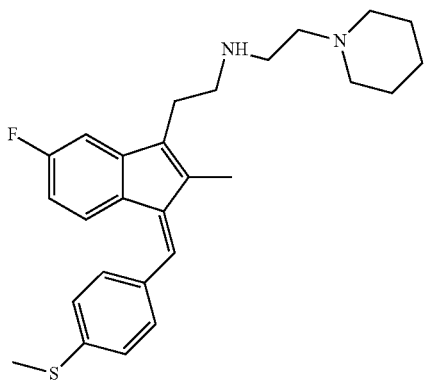 [SMILES: CSc1ccc(/C=C2/C(C)=C(CCNCCN3CCCCC3)c3cc(F)ccc32)cc1] | 6.4 | 5.3 | 4.8 |

TABLE 1-continued
Colon tumor cell growth inhibitory activity of sulindac amine derivatives and reductive amination products.
Results from three human colon tumor cell lines are shown in the Tables shown below.
| | | | | |
|---|---|---|---|---|
| 4 | 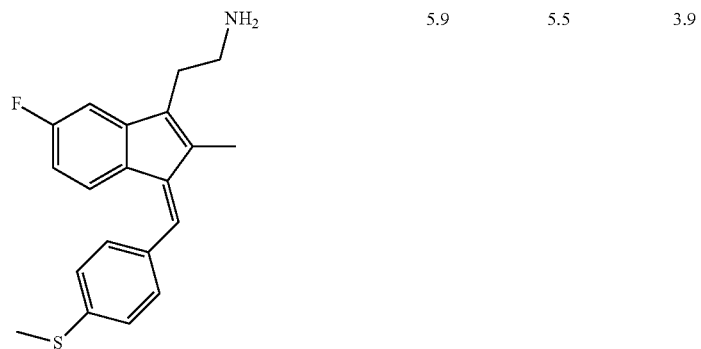 | 5.9 | 5.5 | 3.9 |
| 5 | 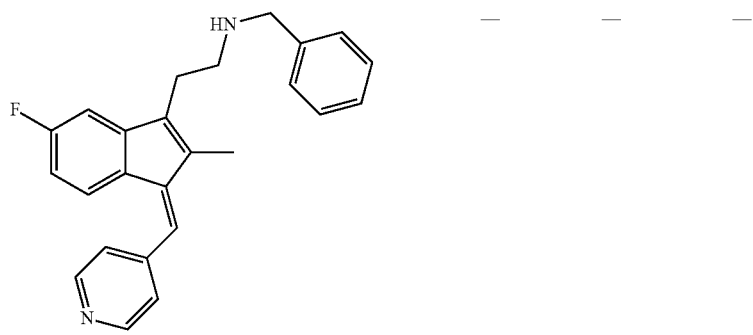 | — | — | — |
| 6 | 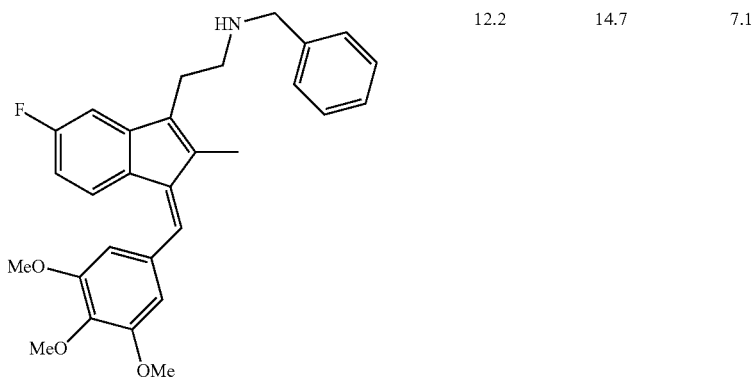 | 12.2 | 14.7 | 7.1 |
| 7 | 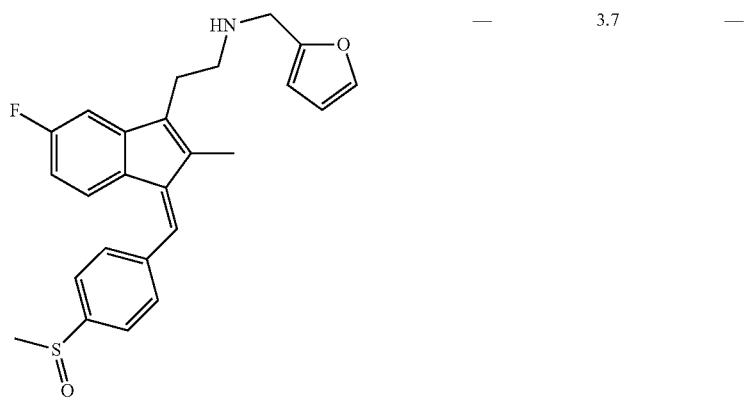 | — | 3.7 | — |

TABLE 1-continued

Colon tumor cell growth inhibitory activity of sulindac amine derivatives and reductive amination products.
Results from three human colon tumor cell lines are shown in the Tables shown below.

| 8 | 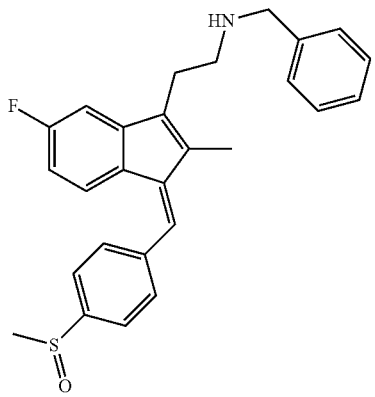 [SMILES: CC1=C(CCNCc2ccccc2)c2cc(F)ccc2/C1=C\c1ccc(S(C)=O)cc1] | — | 6.9 | 5.9 |

— = Not tested

As mentioned herein above, a unique characteristic of the disclosed compounds is that they lack inhibitory effects on cyclooxygenase, types 1 and 2, enzymes, that otherwise would result in the depletion of physiologically important prostaglandins, which can result in gastrointestinal, renal and cardiovascular toxicity. This property is illustrated in FIG. 1 by comparing the ability of a NSAID, such as sulindac sulfide to inhibit the enzymatic activity of cyclooxygenases, types 1 and 2, while a trimethoxy benzyl amino derivative of sulindac referred to as Compound 6 herein with the aforementioned properties lacks this activity. FIG. 1 demonstrates the cyclooxygenase COX-1 and -2 inhibitory activity of the NSAID, sulindac sulfide (SS), and the lack of this effect from Compound 6, an amino derivative of sulindac. The enzyme activity was measured using a colorimetric assay using recombinant COX enzymes. $IC_{50}$ values (50% inhibitory concentration) are listed for each COX isozyme. FIG. 2 shows tumor cell growth inhibitory activity of a trimethoxy amino derivative of sulindac (Compound 6) and sulindac sulfide (SS) against the human MDA-MB-231 breast tumor cell line. The growth inhibitory activity was determined following 72 hours of treatment using a standard cell viability assay (Cell Titer Glo, Promega Corp).

The unexpected improvement in potency of Compound 6 to inhibit tumor cell growth compared with sulindac sulfide is another advantage of such compounds as shown in FIG. 2 and Tables 2 and 3. Another aspect is that the disclosed compounds were found to display potent tumor cell growth inhibitory activity against a variety of tumor cells types derived from solid tumors and hematological malignancies as illustrated in Table 2 by the sensitivity of human tumor cell lines from the "NCI-60" panel to Compound 6. The sensitivity of human colon tumor cell lines derived from adenomas (precancerous lesions) or adenocarcinomas (malignant lesions) to various amino derivatives of sulindac is shown in Table 3.

TABLE 2

Broad spectrum tumor cell growth inhibitory activity of Compound 6 in human tumor cell lines from the "NCI-60 panel"

| Origin | Cell Line | Compound 6 $IC_{50}$ (μM) |
|---|---|---|
| Hematopoietic | CCFR-CEM | 1.70 |
| | SR | 0.96 |
| | HL-60(TB) | 1.47 |
| | K562 | 1.27 |
| | RPMI-8226 | 1.45 |
| | MOLT-4 | 1.29 |
| Colon | HCT-15 | 1.80 |
| | HCT-116 | 2.90 |
| | HCC-2998 | 2.14 |
| | KM12 | 2.31 |
| | SW-620 | 2.62 |
| | COL0205 | 2.47 |
| | HT29 | 1.91 |
| Lung | NCI-H522 | 1.79 |
| | NCI-H460 | 1.86 |
| | NCI-H322M | 3.51 |
| | NCI-H23 | 3.03 |
| | NCI-H226 | 2.44 |
| | A549 | 2.50 |
| | EKVX | 3.77 |
| | HOP-62 | 2.71 |
| | HOP-92 | 2.52 |
| Renal | ACHN | 2.67 |
| | UO-31 | 2.79 |
| | CAKI-1 | 3.51 |
| | A498 | 2.85 |
| | RXF-393 | 2.65 |
| | SN12C | 2.90 |
| | 786-0 | 2.44 |
| | TK-10 | 2.57 |
| Breast | T-47D | 1.44 |
| | MDA-MB-231 | 2.10 |
| | MDA-MB-468 | 2.62 |
| | BT-549 | 2.89 |
| | Hs578T | 1.96 |
| | MCF-7 | 2.40 |
| Other | NCI-ADR/RES | 2.17 |
| Renal | ACHN | 2.67 |
| | UO-31 | 2.79 |
| | CAKI-1 | 3.51 |
| | A498 | 2.85 |
| | RXF-393 | 2.65 |
| | SN12C | 2.90 |
| | 786-0 | 2.44 |
| | TK-10 | 2.57 |

TABLE 2-continued

Broad spectrum tumor cell growth inhibitory activity of Compound 6 in human tumor cell lines from the "NCI-60 panel"

| Origin | Cell Line | Compound 6 IC$_{50}$ (μM) |
|---|---|---|
| Breast | T-47D | 1.44 |
| | MDA-MB-231 | 2.10 |
| | MDA-MB-468 | 2.62 |
| | BT-549 | 2.89 |
| | Hs578T | 1.96 |
| | MCF-7 | 2.40 |
| Ovarian | OVCAR-5 | 1.91 |
| | OVCAR-8 | 2.13 |
| | OVCAR-4 | 3.39 |
| | OVCAR-3 | 2.00 |
| | IGROV-1 | 2.31 |
| | SK-OV-3 | 3.21 |
| Prostate | DU-145 | 5.56 |
| | PC-3 | 2.74 |
| Melanoma | UACC-62 | 2.01 |
| | UACC-257 | 2.16 |
| | LOX IMV1 | 2.82 |
| | M14 | 1.31 |
| | MALME-3M | 2.88 |
| | MDA-MB-435 | 1.02 |
| | SK-MEL-2 | 3.55 |
| | SK-MEL-5 | 1.83 |
| | SK-MEL-28 | 2.04 |
| CNS | SNB-75 | 2.65 |
| | U251 | 1.99 |
| | SF-268 | 2.86 |
| | SNB-19 | 2.72 |
| | SF-539 | 1.67 |
| | SF-295 | 1.36 |

Cells were seeded into 96-well tissue culture treated microtiter plates at a density of 5000-20000 cells/well (depending on cell line) in a total volume of 50 RPMI-1640 containing 10% fetal bovine serum was used as assay media for all the cell lines. After overnight incubation, the cells were treated with SR1 21882 for 72 h by adding 50 μl of 2× stock solutions to appropriate wells already containing 50 μl of cells and medium to expose cells to the final concentrations of compounds required. Cell viability was measured by the Cell Titer Glo Assay (Promega).

TABLE 3

Tumor cell growth inhibitory activity of a series of amino derivatives of sulindac.

| No. | Structure | HT29 (IC$_{50}$) | SW480 (IC$_{50}$) | HCT116 (IC$_{50}$) | LT97 (IC$_{50}$) | FHC (IC$_{50}$) | Colo741 (IC$_{50}$) | Cox-1/-2 Inhibition (IC$_{50}$) |
|---|---|---|---|---|---|---|---|---|
| Sulindac sulfide | 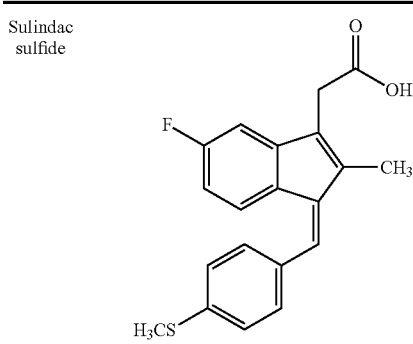 | 73.6 | 85.2 | 73.3 | 37.8 | >200 | 149.9 | 3.35/ 9.68 |
| 1 | 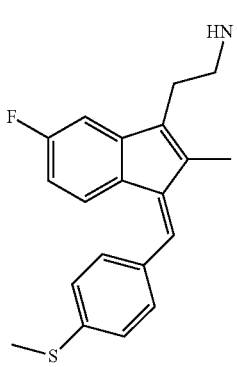 | 2.67 | 3.28 | 4.93 | 6.82 | 7.83 | 8.85 | >200/ >200 |

TABLE 3-continued

Tumor cell growth inhibitory activity of a series of amino derivatives of sulindac.

| No. | Structure | HT29 (IC$_{50}$) | SW480 (IC$_{50}$) | HCT116 (IC$_{50}$) | LT97 (IC$_{50}$) | FHC (IC$_{50}$) | Colo741 (IC$_{50}$) | Cox-1/-2 Inhibition (IC$_{50}$) |
|---|---|---|---|---|---|---|---|---|
| 8 | 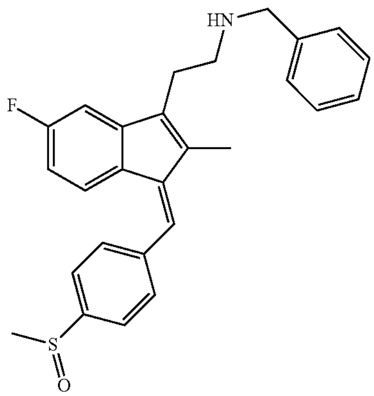 [SMILES: CC1=C(CCNCc2ccccc2)c2cc(F)ccc2/C1=C\c1ccc(S(C)=O)cc1] | 3.14 | 10.70 | 12.47 | 35.2 | 17.42 | 12.85 | >200/>200 |
| 9 | 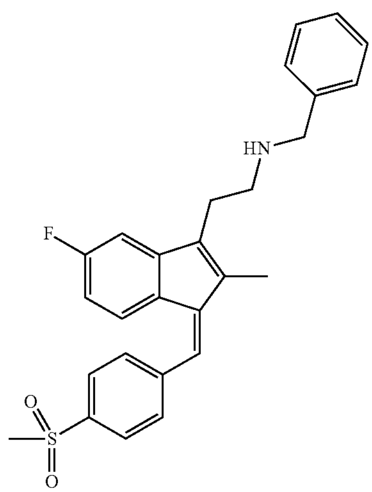 [SMILES: CC1=C(CCNCc2ccccc2)c2cc(F)ccc2/C1=C\c1ccc(S(C)(=O)=O)cc1] | 2.02 | 5.36 | 6.44 | 8.85 | 11.18 | 5.87 | >100/>100 |
| 6 | 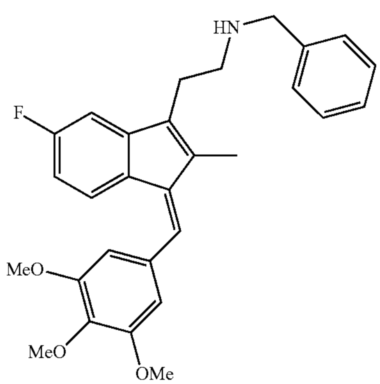 [SMILES: COc1cc(/C=C2/C(C)=C(CCNCc3ccccc3)c3cc(F)ccc32)cc(OC)c1OC] | 5.21 | 2.90 | 3.76 | 5.30 | 3.71 | 5.35 | >100/>100 |

The potency to inhibit tumor cell growth was determined by calculating IC$_{50}$ values using a standard cell viability assay (Cell Titer Glo, Promega Corp,) following 72 hours of treatment. The human colon tumor cell lines, HT-29, SW480, HCT116, and Colo 741 were derived from colon adenocarcinomas, while LT97 is derived from an adenoma. Fetal human colonocytes (FHC) are representative of normal colonocytes. The lack of effect inhibiting cyclooxygenases 1 and 2 (COX-1 and -2) is also shown. Sulindac sulfide is shown for comparison.

It has also been noted according to the present disclosure that amino derivatives according to the present disclosure have the ability to activate cGMP signaling in tumor cells and suppress oncogenic β-catenin transcriptional activity and have shown desirable pharmacokinetic properties in mice.

In keeping with the present disclosure, the derivatives of sulindac can be used alone or in appropriate association, and also may be used in combination with pharmaceutically acceptable carriers and other pharmaceutically active compounds such as various cancer treatment drugs including NSAIDs and/or along with radiation. The active agent may be present in the pharmaceutical composition in any suitable quantity.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, the addition to the active ingredient in an inert base, such as gelatin and glycerin, or sucrose and acadia, emulsions, and gels containing, in addition to the active ingredient, such carriers as are known in the art.

The derivatives of sulindac alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcelluslose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example. dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-does or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, 4$^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

The present disclosure further provides a method of treating precancerous conditions or dysplosia (i.e.—intraepithelial neoplasia) as well as cancer in a mammal, especially humans. The method comprises administering an effective treatment amount of a derivative of sulindac disclosed above to the mammal.

As regards these applications, the present method includes the administration to an animal, particularly a mammal, and more particularly a human, of a therapeutically effective amount of the compound effective in the inhibition of neoplasia and tumor growth and treating malignant disease including metastases, especially colorectal cancer. The method also includes the administration of a therapeutically effect amount of the compound for the treatment of and precancerous lesions such as adenomatous polyps of the colon and other dysplastic lesions of the skin (actinic keratosis), bladder, cervix, esophagus, oral cavity, lung, prostate and breast sometimes referred to as intraepithelial neoplasia.

The disclosed compounds and compositions can be administered to treat a number of cancers, including leukemias and lymphomas such as acute lymphocytic leukemia, acute non-lymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms Tumor, bone tumors, and soft-tissue sarcomas, common solid tumors of adults such as lung cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer.

The present disclosure also relates to treating certain chronic inflammatory conditions which NSAIDs have shown benefit, but may be contraindicated due to cyclooxygenase inhibition (i.e.—inflammatory bowel disease) or do not appear to require cyclooxygenase inhibition for efficacy such as certain neurodegenerative diseases, including Alzheimer's disease. Still there are additional disease indications that benefit from treatment with NSAIDs, which can also be treated or prevented with compounds described in the present disclosure.

The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the cancer.

A suitable dose is that which will result in a concentration of the active agent in tumor tissue which is known to affect the desired response. The preferred dosage is the amount which results in maximum inhibition of cancer, without unmanageable side effects.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

The method disclosed comprises further administering of chemotherapeutic agent other than the derivatives of the present invention. Any suitable chemotherapeutic agent can be employed for this purpose. The chemotherapeutic agent is typically selected from the group consisting of alkylating agents, antimetabolites, natural products, anti-inflammatory agents, hormonal agents, molecular targeted drugs, anti-angiogenic drugs, and miscellaneous agents.

Examples of alkylating chemotherapeutic agents include carmustine, chlorambucil, cisplatin, lomustine, cyclophosphamide, melphalan, mechlorethamine, procarbazine, thiotepa, uracil mustard, triethylenemelamine, busulfan, pipobroman, streptozocin, Ifosfamide, dacarbazine, carboplatin, and hexamethylmelamine.

Examples of chemotherapeutic agents that are antimetabolites include cytosine arabinoside fluorouracil, gemcitabine, mercaptopurine, methotrexate, thioguanine, floxuridine, fludarabine, and cladribine.

Examples of chemotherapeutic agents that are natural products include actinomycin D, bleomycin, camptothecins, daunomycin, doxorubicin, etoposide, mitomycin C, paclitaxel, taxoteredocetaxel, tenisposide, vincristine, vinblastine, vinorelbine, idarubicin, mitoxantrone, mithramycin and deoxycoformycin.

Examples of hormonal agents include estrogen receptor antagonists such as tamoxifen and fluvestrant, aromatase inhibitors such as anastrozole, androgen receptor antagonists such as cyproterone and flutamine, as well as gonadotropin release hormone agonists such as leuprolide. Examples of anti-inflammatory drugs include adrenocorticoids such as prednisone, and nonsteroidal anti-inflammatory drugs such as sulindac or celecoxib. Examples of molecular targeted drugs include monoclonal antibodies such as rituximab, cetuximab, trastuzumab and small molecules such as imatinib, erlotinib, ortizumib. Examples of anti-angiogenic drugs include thalidomide and bevacizimab. Examples of the aforesaid miscellaneous chemotherapeutic agents include mitotane, arsenic trioxide, tretinoin, thalidomide, levamisole, L-asparaginase and hydroxyurea.

Exemplary embodiments of the present disclosure include:

Embodiment A

Compound represented by the formula

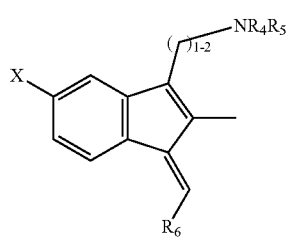

wherein each of $R_4$ and $R_5$ is selected from the group consisting of H, alkyl, a substituted or unsubstituted 5 or 6 member ring, provided that at least one of $R_4$ and $R_5$ is other than H; and when both $R_1$ and $R_5$ are a substituted or unsubstituted 5 or 6 member ring, both of $R_4$ and $R_5$ are a substituted or unsubstituted pyridyl ring;

$R_6$ is a substituted or unsubstituted 5 or 6 member ring;

X is a halogen; and pharmaceutically acceptable salts thereof, prodrugs thereof, solvates thereof and mixtures thereof.

Embodiment B

The compound of Embodiment A being represented by the following formula:

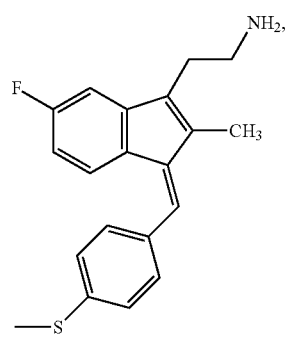 [SMILES: CSc1ccc(/C=C2/C(C)=C(CCN)c3cc(F)ccc32)cc1]

pharmaceutically acceptable salts thereof, prodrugs thereof, solvates thereof and mixtures thereof.

Embodiment C

The compound of Embodiment A being represented by the following formula:

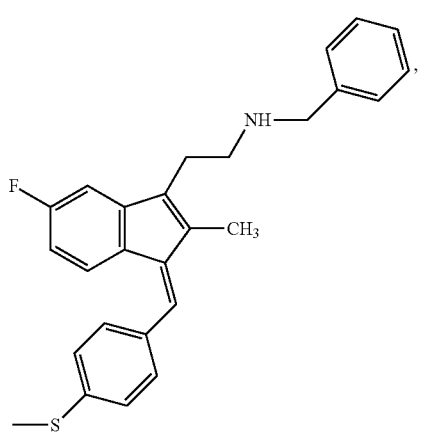 [SMILES: CSc1ccc(/C=C2/C(C)=C(CCNCc3ccccc3)c3cc(F)ccc32)cc1]

pharmaceutically acceptable salts thereof, prodrugs thereof, solvates thereof and mixtures thereof.

Embodiment D

The compound of Embodiment A being represented by the following formula:

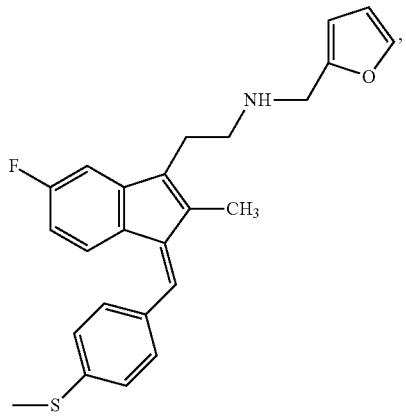 [SMILES: CSc1ccc(/C=C2/C(C)=C(CCNCc3ccco3)c3cc(F)ccc32)cc1]

pharmaceutically acceptable salts thereof, prodrugs thereof, solvates thereof and mixtures thereof.

Embodiment E

The compound of Embodiment A being represented by the following formula:

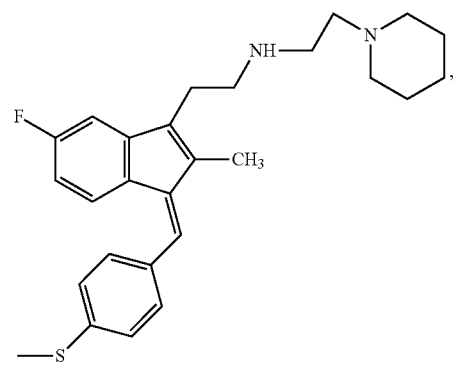 [SMILES: CSc1ccc(/C=C2/C(C)=C(CCNCCN3CCCCC3)c3cc(F)ccc32)cc1]

pharmaceutically acceptable salts thereof, prodrugs thereof, solvates thereof and mixtures thereof.

Embodiment F

The compound of Embodiment A represented by the following formula:

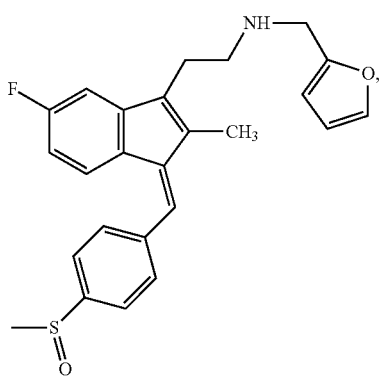 [SMILES: CC1=C(CCNCc2ccco2)c2cc(F)ccc2/C1=C\c1ccc(S(C)=O)cc1]

pharmaceutically acceptable salts thereof, prodrugs thereof, solvates thereof and mixtures thereof.

Embodiment G

The compound of Embodiment A being represented by the following formula:

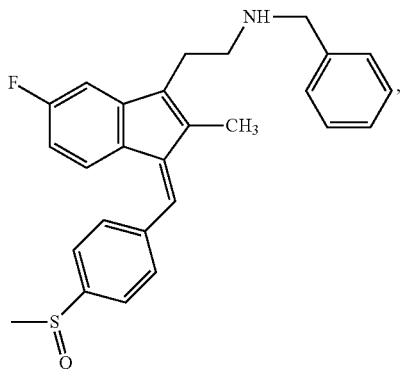 [SMILES: CC1=C(CCNCc2ccccc2)c2cc(F)ccc2/C1=C\c1ccc(S(C)=O)cc1]

pharmaceutically acceptable salts thereof, prodrugs thereof, solvates thereof and mixtures thereof.

Embodiment H

The compound of Embodiment A being represented by the following formula:

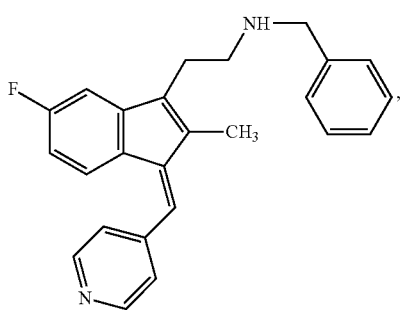

pharmaceutically acceptable salts thereof, prodrugs thereof, solvates thereof and mixtures thereof.

Embodiment I

The compound of Embodiment A being represented by the following formula:

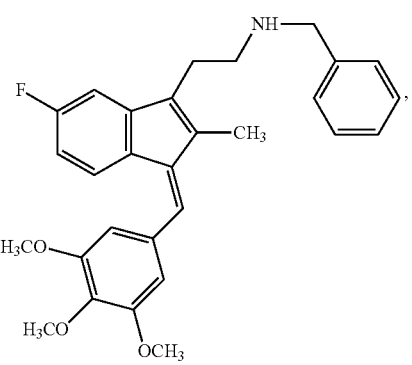 [SMILES: COc1cc(/C=C2/C(C)=C(CCNCc3ccccc3)c3cc(F)ccc32)cc(OC)c1OC]

pharmaceutically acceptable salts thereof, prodrugs thereof, solvates thereof and mixtures thereof.

Embodiment J

The compound of Embodiment A being represented by the following formula:

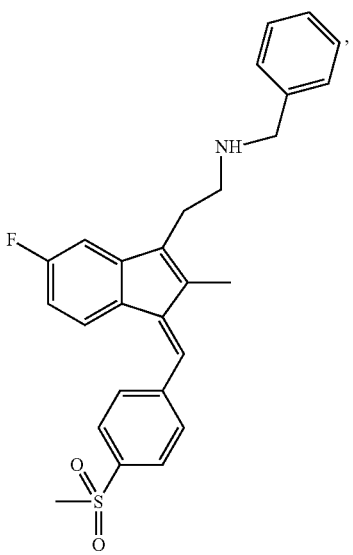 [SMILES: CC1=C(CCNCc2ccccc2)c2cc(F)ccc2/C1=C\c1ccc(S(C)(=O)=O)cc1]

pharmaceutically acceptable salts thereof, prodrugs thereof, solvates thereof and mixtures thereof.

Embodiment K

The compound of Embodiment A being represented by the following formula:

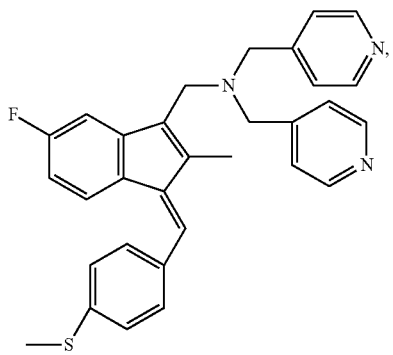 [SMILES: CSc1ccc(/C=C2/C(C)=C(CN(Cc3ccncc3)Cc3ccncc3)c3cc(F)ccc32)cc1]

pharmaceutically acceptable salts thereof, prodrugs thereof, solvates thereof and mixtures thereof.

Embodiment L

A compound being represented by the following formula:

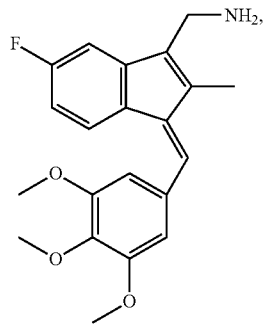 [SMILES: COc1cc(/C=C2/C(C)=C(CN)c3cc(F)ccc32)cc(OC)c1OC]

pharmaceutically acceptable salts thereof, prodrugs thereof, solvates thereof and mixtures thereof,

Embodiment M

The compound of Embodiment A being represented by the following formula:

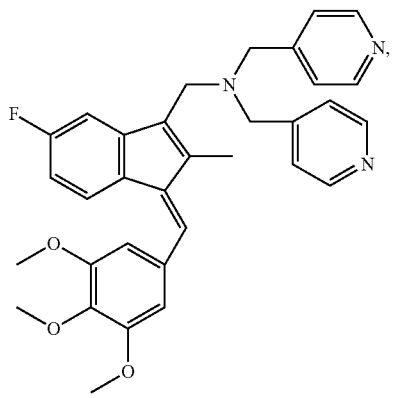 [SMILES: COc1cc(/C=C2/C(C)=C(CN(Cc3ccncc3)Cc3ccncc3)c3cc(F)ccc32)cc(OC)c1OC]

pharmaceutically acceptable salts thereof, prodrugs thereof, solvates thereof and mixtures thereof.

Embodiment N

A pharmaceutical composition comprising a compound represented by the formula:

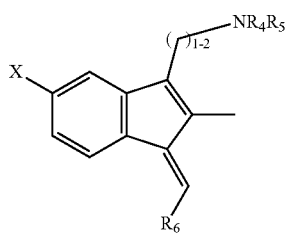

wherein each of $R_4$ and $R_5$ is selected from the group consisting of H, alkyl, a substituted or unsubstituted 5 or 6 member ring, provided that at least one of $R_4$ and $R_5$ is other than H; and when both $R_4$ and $R_5$ are a substituted or unsubstituted 5 or 6 member ring, both of $R_4$ and $R_5$ are a substituted or unsubstituted pyridyl ring;

$R_6$ is a substituted or unsubstituted 5 or 6 member ring; and

X is a halogen; and/or a compound according to any one of Embodiments A-M, pharmaceutically acceptable salts thereof, prodrugs thereof, solvates thereof and mixtures thereof;

and a pharmaceutically acceptable carrier.

Embodiment O

A method of treating a precancerous condition or cancer in a mammal comprising administering to the mammal an effective treatment amount of a compound represented by the formula:

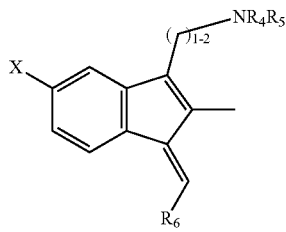

wherein each of $R_4$ and $R_5$ is selected from the group consisting of H, alkyl, a substituted or unsubstituted 5 or 6 member ring, provided that at least one of $R_4$ and $R_5$ is other than H; and when both $R_4$ and $R_5$ are a substituted or unsubstituted 5 or 6 member ring, both of $R_4$ and $R_5$ are a substituted or unsubstituted pyridyl ring;

$R_6$ is a substituted or unsubstituted 5 or 6 member ring; and

X is a halogen; and/or a compound according to any one of Embodiments A-M, pharmaceutically acceptable salts thereof, prodrugs thereof, solvates thereof and mixtures thereof.

Embodiment P

A method for treating a patient with a chronic inflammatory disease, which comprises administering to the patient an effective treatment amount of a compound represented by the formula:

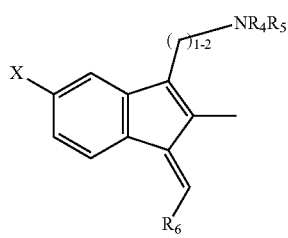

wherein each of $R_4$ and $R_5$ is selected from the group consisting of H, alkyl, a substituted or unsubstituted 5 or 6 member ring, provided that at least one of $R_4$ and $R_5$ is other than H; and when both $R_4$ and $R_5$ are a substituted or unsubstituted 5 or 6 member ring, both of $R_4$ and $R_5$ are a substituted or unsubstituted pyridyl ring;

$R_6$ is a substituted or unsubstituted 5 or 6 member ring; and

X is a halogen; and/or a compound according to any one of Embodiments A-M, pharmaceutically acceptable salts thereof, prodrugs thereof, solvates thereof and mixtures thereof.

Embodiment Q

The method according to Embodiment P, wherein the chronic inflammatory disease is inflammatory bowel disease.

Embodiment R

A method for treating a patient having a neurodegenerative disease, which comprises administering to the patient an effective treatment amount of a compound represented by the formula:

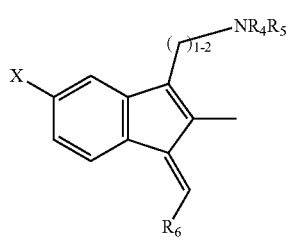

wherein each of $R_4$ and $R_5$ is selected from the group consisting of H, alkyl, a substituted or unsubstituted 5 or 6 member ring, provided that at least one of $R_4$ and $R_5$ is other than H; and when both $R_4$ and $R_5$ are a substituted or unsubstituted 5 or 6 member ring, both of $R_4$ and $R_5$ are a substituted or unsubstituted pyridyl ring;

$R_6$ is a substituted or unsubstituted 5 or 6 member ring; and

X is a halogen; and/or a compound according to any one of Embodiments A-M, pharmaceutically acceptable salts thereof, prodrugs thereof, solvates thereof and mixtures thereof.

Embodiment S

The method according to Embodiment R, wherein the neurodegenerative disease is Alzheimer's disease.

Embodiment T

A method for preparing a compound according to any one of Embodiments A-K and M which comprise converting an ester of sulindac or a derivative therefore represented by the following formula:

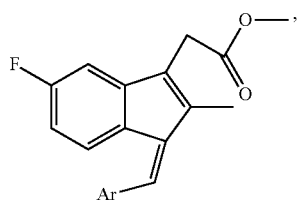

wherein Ar is a substituted or unsubstituted 5 or 6 member ring compound to obtain an aldehyde represented by the following formula;

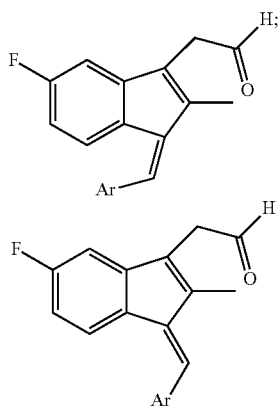

reacting the aldehyde with ammonia or an amine represented by $R_4R_5NH$, wherein each $R_4$ and $R_5$ is at least one member selected from the group consisting of H, alkyl, a substituted or unsubstituted 5 or 6 member ring; and when both $R_4$ and $R_5$ are a substituted or unsubstituted 5 or 6 member ring, both of $R_4$ and $R_5$ are a substituted or unsubstituted pyridyl ring.

The term "comprising" (and its grammatical variations) as used herein is used in the inclusive sense of "having" or "including" and not in the exclusive sense of "consisting only of." The terms "a", "an" and "the" as used herein are understood to encompass the plural as well as the singular, unless indicated otherwise.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

REFERENCES

1. Jemal A, Siegel R, Xu J, Ward E. Cancer statistics, 2010. CA Cancer J Clin 2010; 60: 277-300.
2. Anderson J C. Risk factors and diagnosis of flat adenomas of the colon. Expert Rev Gastroenterol Hepatol 2011; 5: 25-32.
3. Johnson M D, Mackey R, Brown N, Church J, Burke C, Walsh R M. Outcome based on management for duodenal adenomas: sporadic versus familial disease. J Gastrointest Surg 2010; 14: 229-35.
4. Garcia-Rodriguez L A, Huerta-Alvarez C. Reduced risk of colorectal cancer among long-term users of aspirin and nonaspirin nonsteroidal anti inflammatory drugs. Epidemiology 2001; 12: 88-93.
5. Giardiello F M, Hamilton S R, Krush A J, Piantadosi S, Hylind L M, Celano P, et al. Treatment of colonic and rectal adenomas with sulindac in familial adenomatous polyposis. N Engl J Med 1993; 328: 1313-6.
6. Rigas B, Goldman I S, Levine L. Altered eicosanoid levels in human colon cancer. J Lab Clin Med 1993; 122: 518-23.
7. Eberhart C E, Coffey R J, Radhika A, Giardiello F M, Ferrenbach S, DuBois R N. Up-regulation of cyclooxygenase 2 gene expression in human colorectal adenomas and adenocarcinomas. Gastroenterology 1994; 107: 1183-8.
8. Hwang D H, Fung V, Dannenberg A J. National Cancer Institute workshop on chemopreventive properties of nonsteroidal anti-inflammatory drugs: role of COX-dependent and -independent mechanisms. Neoplasia 2002; 4: 91-7.
9. Rigas B, Kashfi K. Cancer prevention: a new era beyond cyclooxygenase-2. J Pharmacol Exp Ther 2005; 314: 1-8.
10. Alberts D S, Hixson L, Ahnen D, Bogert C, Einspahr J, Paranka N, et al. Do NSAIDs exert their colon cancer chemoprevention activities through the inhibition of mucosal prostaglandin synthetase? J Cell Biochem Suppl 1995; 22: 18-23.
11. Piazza G A, Rahm A L, Krutzsch M, Sperl G, Paranka N S, Gross P H, et al. Antineoplastic drugs sulindac sulfide and sulfone inhibit cell growth by inducing apoptosis. Cancer Res 1995; 55: 3110-6.

12. Piazza G A, Rahm A K, Finn T S, Fryer B H, Li H, Stoumen A L, et al. Apoptosis primarily accounts for the growth-inhibitory properties of sulindac metabolites and involves a mechanism that is independent of cyclooxygenase inhibition, cell cycle arrest, and p53 induction. Cancer Res 1997; 57: 2452-9.
13. Piazza G A, Alberts D S, Hixson L J, Paranka N S, Li H, Finn T, et al. Sulindac sulfone inhibits azoxymethane-induced colon carcinogenesis in rats without reducing prostaglandin levels. Cancer Res 1997; 57: 2909-15.
14. Charalambous D, O'Brien P E. Inhibition of colon cancer precursors in the rat by sulindac sulphone is not dependent on inhibition of prostaglandin synthesis. J Gastroenterol Hepatol 1996; 11: 307-10.
15. Reddy B S, Kawamori T, Lubet R A, Steele V E, Kelloff G J, Rao C V. Chemopreventive efficacy of sulindac sulfone against colon cancer depends on time of administration during carcinogenic process. Cancer Res 1999; 59: 3387-91.
16. Stoner G D, Budd G T, Ganaphthi R, DeYoung B, Kresty L A, Nitert M, et al. Sulindac sulfone induced regression of rectal polyps in patients with familial adenomatous polyposis. Adv Exp Med Biol 1999; 470: 45-53.
17. Arber N, Kuwada S, Leshno M, Sjodahl R, Hultcrantz R, Rex D. Sporadic adenomatous polyp regression with exisulind is effective but toxic: a randomised, double blind, placebo controlled, dose-response study. Gut 2006; 55: 367-73.
18. Huang E S, Strate L L, Ho W W, Lee S S, Chan A T. Long-term use of aspirin and the risk of gastrointestinal bleeding. Am J Med 2011; 124: 426-33.
19. Mukherjee D, Nissen S E, Topol E J. Risk of cardiovascular events associated with selective COX-2 inhibitors. Jama 2001; 286: 954-9.
20. Koornstra J J, Rijcken F E, Oldenhuis C N, Zwart N, van der Sluis T, Hollema H, et al. Sulindac inhibits beta-catenin expression in normal-appearing colon of hereditary non-polyposis colorectal cancer and familial adenomatous polyposis patients. Cancer Epidemiol Biomarkers Prev 2005; 14: 1608-12.
21. Boon E M, Keller J J, Wormhoudt T A, Giardiello F M, Offerhaus G J, van der Neut R, et al. Sulindac targets nuclear beta-catenin accumulation and Wnt signalling in adenomas of patients with familial adenomatous polyposis and in human colorectal cancer cell lines. Br J Cancer 2004; 90: 224-9.
22. Rice P L, Kelloff J, Sullivan H, Driggers L J, Beard K S, Kuwada S, et al. Sulindac metabolites induce caspase- and proteasome-dependent degradation of beta-catenin protein in human colon cancer cells. Mol Cancer Ther 2003; 2: 885-92.
23. Thompson W J, Piazza G A, Li H, Liu L, Fetter J, Zhu B, et al. Exisulind induction of apoptosis involves guanosine 3',5'-cyclic monophosphate phosphodiesterase inhibition, protein kinase G activation, and attenuated beta-catenin. Cancer Res 2000; 60: 3338-42.
24. Clapper M L, Coudry J, Chang W C. beta-catenin-mediated signaling: a molecular target for early chemopreventive intervention, Mutat Res 2004; 555: 97-105.
25. Piazza G A, Thompson W J, Pamukcu R, Alila H W, Whitehead C M, Liu L, et al. Exisulind, a novel proapoptotic drug, inhibits rat urinary bladder tumorigenesis. Cancer Res 2001; 61: 3961-8.
26. Tinsley H N, Gary B D, Keeton A B, Zhang W, Abadi A H, Reynolds R C, et al. Sulindac sulfide selectively inhibits growth and induces apoptosis of human breast tumor cells by phosphodiesterase 5 inhibition, elevation of cyclic GMP, and activation of protein kinase G. Mol Cancer Ther 2009; 8: 3331-40.
27. Tinsley H N, Gary B D, Thaiparambil J, Li N, Lu W, Li Y, et al. Colon tumor cell growth-inhibitory activity of sulindac sulfide and other nonsteroidal anti-inflammatory drugs is associated with phosphodiesterase 5 inhibition. Cancer Prev Res (Phila) 2010; 3: 1303-13.
28. Tinsley H N, Gary B D, Keeton A B, Lu W, Li Y, Piazza G A. Inhibition of PDE5 by Sulindac Sulfide Selectively Induces Apoptosis and Attenuates Oncogenic Wnt/{beta}-Catenin-Mediated Transcription in Human Breast Tumor Cells. Cancer Prev Res (Phila) 2011; 4: 1275-84.
29. Beavo J A. Cyclic nucleotide phosphodiesterases: functional implications of multiple isoforms. Physiol Rev 1995; 75: 725-48.
30. Lincoln T M, Cornwell T L. Intracellular cyclic GMP receptor proteins. Faseb J 1993; 7: 328-38.

What is claimed is:

1. A compound represented by the formula:

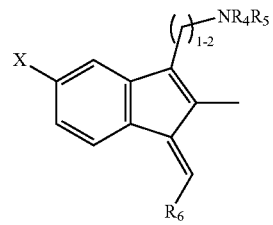

wherein each of $R_4$ and $R_5$ is selected from the group consisting of H, alkyl, a substituted or unsubstituted 5 or 6 member ring and when substituted the 5 or 6 member ring is substituted with at least one member selected from the group consisting of alkyl, halo, alkoxy, amino and aminoalkyl, provided that at least one of $R_4$ and $R_5$ is a substituted or unsubstituted 5 or 6 member ring other than H; and when both $R_4$ and $R_5$ are a substituted or unsubstituted 5 or 6 member ring, both of $R_4$ and $R_5$ are a substituted or unsubstituted pyridyl ring;

$R_6$ is a substituted or unsubstituted 5 or 6 member ring;

X is a halogen; and pharmaceutically acceptable salts thereof, solvates thereof and mixtures thereof.

2. The compound of claim 1 being represented by the following formula:

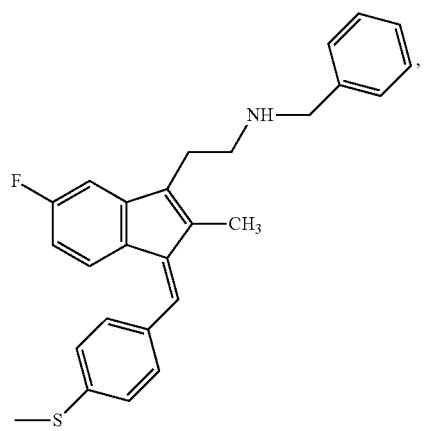

pharmaceutically acceptable salts thereof, solvates thereof and mixtures thereof.

3. The compound of claim 1 being represented by the following formula:

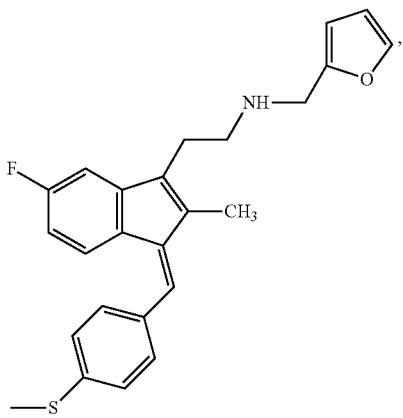 [SMILES: CSc1ccc(/C=C2/C(C)=C(CCNCc3ccco3)c3cc(F)ccc32)cc1]

pharmaceutically acceptable salts thereof, solvates thereof and mixtures thereof.

4. The compound of claim 1 being represented by the following formula:

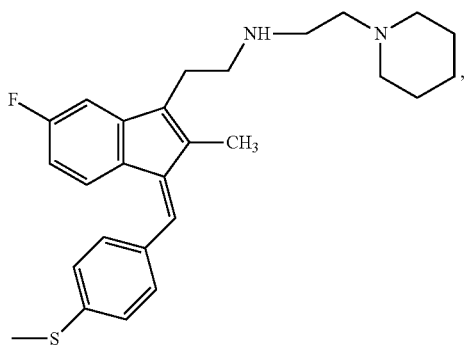 [SMILES: CSc1ccc(/C=C2/C(C)=C(CCNCCN3CCCCC3)c3cc(F)ccc32)cc1]

pharmaceutically acceptable salts thereof, solvates thereof and mixtures thereof.

5. The compound of claim 1 being represented by the following formula:

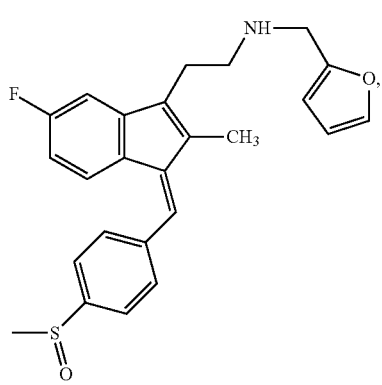 [SMILES: CC1=C(CCNCc2ccco2)c2cc(F)ccc2/C1=C\c1ccc(S(C)=O)cc1]

pharmaceutically acceptable salts thereof, solvates thereof and mixtures thereof.

6. The compound of claim 1 being represented by the following formula:

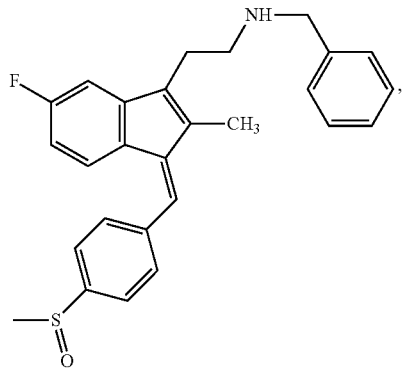 [SMILES: CC1=C(CCNCc2ccccc2)c2cc(F)ccc2/C1=C\c1ccc(S(C)=O)cc1]

pharmaceutically acceptable salts thereof, solvates thereof and mixtures thereof.

7. The compound of claim 1 being represented by the following formula:

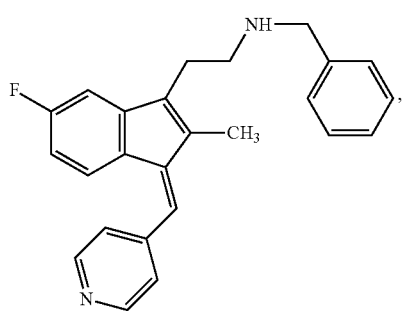 [SMILES: CC1=C(CCNCc2ccccc2)c2cc(F)ccc2/C1=C\c1ccncc1]

pharmaceutically acceptable salts thereof, solvates thereof and mixtures thereof.

8. The compound of claim 1 being represented by the following formula:

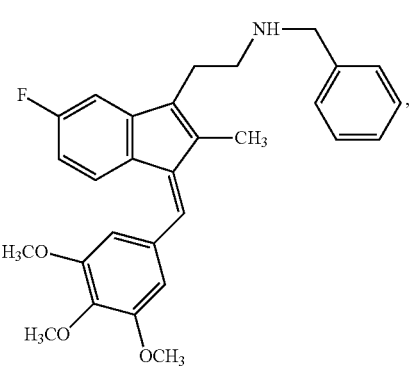 [SMILES: COc1cc(/C=C2/C(C)=C(CCNCc3ccccc3)c3cc(F)ccc32)cc(OC)c1OC]

pharmaceutically acceptable salts thereof, solvates thereof and mixtures thereof.

9. The compound of claim 1 being represented by the following formula:

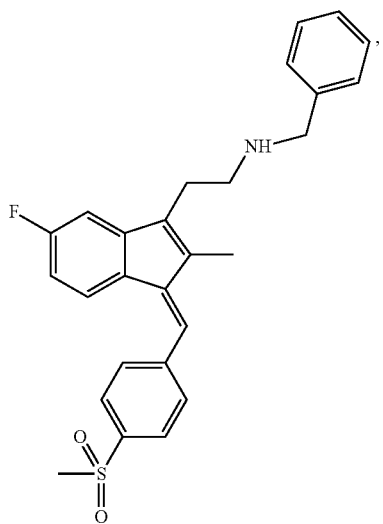 [SMILES: CC1=C(CCNCc2ccccc2)c2cc(F)ccc2/C1=C\c1ccc(S(C)(=O)=O)cc1]

pharmaceutically acceptable salts thereof, solvates thereof and mixtures thereof.

10. The compound of claim 1 being represented by the following formula:

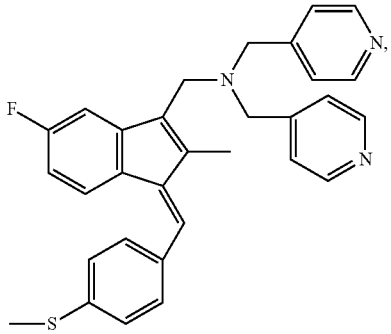 [SMILES: CSc1ccc(/C=C2/C(C)=C(CN(Cc3ccncc3)Cc3ccncc3)c3cc(F)ccc32)cc1]

pharmaceutically acceptable salts thereof, thereof, solvates thereof and mixtures thereof.

11. A compound being represented by the following formula:

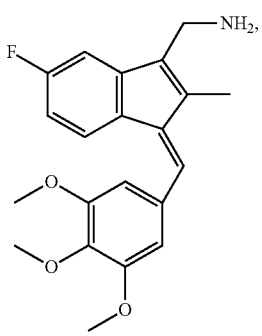 [SMILES: COc1cc(/C=C2/C(C)=C(CN)c3cc(F)ccc32)cc(OC)c1OC]

pharmaceutically acceptable salts thereof, solvates thereof and mixtures thereof.

12. The compound of claim 1 being represented by the following formula:

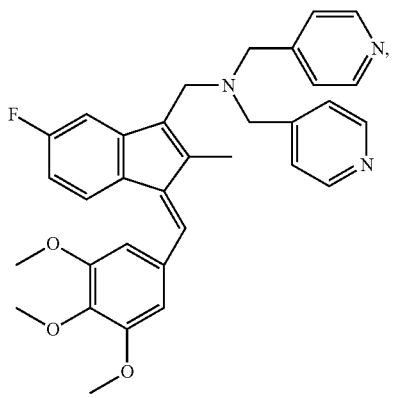

pharmaceutically acceptable salts thereof, solvates thereof and mixtures thereof.

13. A pharmaceutical composition comprising a compound represented by the formula:

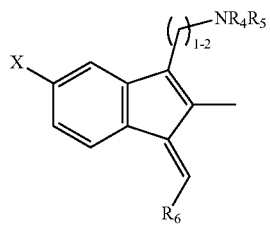

wherein each of $R_4$ and $R_5$ is selected from the group consisting of H, alkyl, a substituted or unsubstituted 5 or 6 member ring and when substituted the 5 or 6 member ring is substituted with at least one member selected from the group consisting of alkyl, halo, alkoxy, amino and aminoalkyl, provided that at least one of $R_4$ and $R_5$ is a substituted or unsubstituted 5 or 6 member ring; and when both $R_4$ and $R_5$ are a substituted or unsubstituted 5 or 6 member ring, both of $R_4$ and $R_5$ are a substituted or unsubstituted pyridyl ring;

$R_6$ is a substituted or unsubstituted 5 or 6 member ring; and

X is a halogen; and pharmaceutically acceptable salts thereof, solvates thereof and mixtures thereof; and a pharmaceutically acceptable carrier.

14. The compound of claim 1, wherein each of $R_4$ and $R_5$ is selected from the group consisting of H, alkyl, or unsubstituted 5 or 6 member ring.

15. The composition of claim 13, wherein each of $R_4$ and $R_5$ is selected from the group consisting of H, alkyl, or unsubstituted 5 or 6 member ring.

\* \* \* \* \*